(12) United States Patent
Mehta et al.

(10) Patent No.: US 9,006,172 B2
(45) Date of Patent: Apr. 14, 2015

(54) PEPTIDE ANALOGS FOR TREATING DISEASES AND DISORDERS

(71) Applicant: KeyBioscience AG, Stans (CH)

(72) Inventors: Nozer M. Mehta, Randolph, NJ (US); William Stern, Tenally, NJ (US); Amy M. Sturmer, Towaco, NJ (US); Morten Asser Karsdal, Copenhagen (DK); Kim Henriksen, Hillerod (DK)

(73) Assignee: KeyBioscience AG, Stans (CH)

( * ) Notice: Subject to any disclaimer, the term of this patent is extended or adjusted under 35 U.S.C. 154(b) by 0 days.

(21) Appl. No.: 13/667,578

(22) Filed: Nov. 2, 2012

(65) Prior Publication Data

US 2013/0183385 A1 Jul. 18, 2013

Related U.S. Application Data

(60) Provisional application No. 61/554,771, filed on Nov. 2, 2011, provisional application No. 61/578,620, filed on Dec. 21, 2011.

(51) Int. Cl.
| | |
|---|---|
| *A61K 38/00* | (2006.01) |
| *A61K 38/23* | (2006.01) |
| *A61P 3/04* | (2006.01) |
| *C07K 5/00* | (2006.01) |
| *C07K 14/585* | (2006.01) |

(52) U.S. Cl.
CPC .............. *C07K 14/585* (2013.01); *A61K 38/23* (2013.01)

(58) Field of Classification Search
CPC combination set(s) only.
See application file for complete search history.

(56) References Cited

U.S. PATENT DOCUMENTS

| 4,708,934 | A | 11/1987 | Gilligan et al. | |
|---|---|---|---|---|
| 5,175,146 | A | 12/1992 | Basava et al. | |
| 5,536,812 | A | 7/1996 | Noda et al. | |
| 5,688,784 | A | 11/1997 | McNeill et al. | |
| 6,420,561 | B1 | 7/2002 | Haruta et al. | |
| 8,076,291 | B2 | 12/2011 | Mehta et al. | |
| 8,217,139 | B2* | 7/2012 | Mehta et al. | 530/323 |
| 8,378,067 | B2 | 2/2013 | Mehta et al. | |
| 8,497,347 | B2* | 7/2013 | Mehta et al. | 530/307 |
| 2001/0031856 | A1* | 10/2001 | Wagner et al. | 530/307 |
| 2002/0065255 | A1* | 5/2002 | Bay et al. | 514/166 |
| 2005/0197287 | A1 | 9/2005 | Mack et al. | |
| 2006/0127995 | A1 | 6/2006 | Consalvo | |
| 2006/0292672 | A1 | 12/2006 | Miller et al. | |
| 2008/0207512 | A1 | 8/2008 | Roth et al. | |
| 2008/0274952 | A1 | 11/2008 | Soares et al. | |
| 2009/0048157 | A1 | 2/2009 | Azria et al. | |
| 2010/0311650 | A1* | 12/2010 | Mehta et al. | 514/4.9 |
| 2012/0142586 | A1 | 6/2012 | Mehta et al. | |
| 2012/0149635 | A1 | 6/2012 | Mehta et al. | |
| 2012/0302497 | A1 | 11/2012 | Mehta et al. | |

FOREIGN PATENT DOCUMENTS

| EP | 0 308 067 A2 | 3/1989 |
|---|---|---|
| EP | 0 382 403 A2 | 8/1990 |
| JP | 2000-290295 A | 10/2000 |
| WO | 96/24618 A1 | 8/1996 |
| WO | 96/40196 A1 | 12/1996 |
| WO | 2006/83254 A1 | 8/2006 |
| WO | 2010/85700 A3 | 7/2010 |
| WO | 2010/103045 A1 | 9/2010 |

OTHER PUBLICATIONS

Feigh et al., "A novel oral form of salmon calcitonin improves glucose homeostasis and reduces body weight in diet-induced obese rats" Diab. Obesity Metab. 13:911-920 (2011).*
Hay, et al. Amylin receptors: molecular composition and pharmacology, Biochem Soc Trans 2004;vol. 32:865-867.
Guggi, et al. In vivo evaluation of an oral salmon calcitonin-delivery system based on a thiolated chitosan carrier matrix, Pharm Res 2003;vol. 20:1989-1994.
Guggi, et al. Systemic peptide delivery via the stomach: in vivo evaluation of an oral dosage form for salmon calcitonin, J Control Release 2003;vol. 92:125-135.
Greeley, et al. Intracerebroventricular administration of calcitonin enhances glucose-stimulated release of insulin, Regul Peptides 1989;vol. 24:259-268.
Giugliano, et al. Calcitonin in diabetes, Lancet 1980:p. 653.
Garcia-Fuentes, et al. A comparative study of the potential of solid triglyceride nanostructures coated with chitosan or poly(ethylene glycol) as carriers for oral calcitonin delivery, Eur J Pharm Sci 2005;vol. 25:133-143.
Eglen, et al. Assessing GPCR activation using protein complementation: a novel technique for HTS, Biochem Soc Trans 2007;vol. 35:746-748.
Dogru, et al. Oral multiple w/o/w emulsion formulation of a peptide salmon calcitonin: in vitro-in vivo evaluation, J Clin Pharm Ther 2000;vol. 25:435-443.
Dacquin, et al. Amylin inhibits bone resorption while the calcitonin receptor controls bone formation in vivo, J Cell Biol 2004;vol. 164:509-514.
Cornish, et al. Effects of calcitonin, amylin, and calcitonin gene-related peptide on osteoclast development, Bone 2001;vol. 29:162-168.
Calceti, et al. Development and in vivo evaluation of an oral insulin—PEG delivery system, Eur J Pharm Sci 2004;22:315-323.

(Continued)

*Primary Examiner* — Julie Ha
*Assistant Examiner* — Kristina M Hellman
(74) *Attorney, Agent, or Firm* — Benjamin Aaron Adler

(57) ABSTRACT

A peptide having a sequence selected from SEQ ID NO:11, SEQ ID NO:12, SEQ ID NO:13, SEQ ID NO:14, SEQ ID NO:15, SEQ ID NO:16, SEQ ID NO:17 and SEQ ID NO:18. Said peptide used for the treatment of type I diabetes, Type II diabetes, metabolic syndrome, or obesity, or of appetite suppression, or for mitigating insulin resistance, or for reducing an undesirably high fasting serum glucose level, or for reducing an undesirably high peak serum glucose level, or for reducing an undesirably high peak serum insulin level, or for reducing an undesirably large response to a glucose tolerance test.

18 Claims, 22 Drawing Sheets

(56) References Cited

OTHER PUBLICATIONS

Beukers, et al. Techniques: how to boost GPCR mutagenesis studies using yeast, Trends Pharmacol Sci 2005; vol. 26:533-539.

Bernkop-Schnurch, et al. The use of thiolated polymers as carrier matrix in oral peptide delivery-proof of concept, J Control Release 2005;106:26-33.

Arvinte, et al. Comparative study of human and salmon calcitonin secondary structure in solutions with low dielectric constants, J Biol Chem 1993;vol. 268:6408-6414.

Bello, et al. Salmon calcitonin reduces food intake through changes in meal sizes in male rhesus monkeys, Am J Physiol Regul Integr Comp Physiol 2008;vol. 295:R76-R81.

Albrandt, et al. Molecular cloning of two receptors from rat brain with high affinity for salmon calcitonin, FEBS 1993; vol. 325:225-232.

Zofkova, et al. Comparison of metabolic and hormonal effects of calcitonin and somatostatin (SRIF) in the course of oral glucose tolerance test (OGTT), Horm Metabol Res 1987;vol. 19:656-660.

Zofkova, et al. The effects of calcitonin, somatostatin and hypercalcaemia on metabolic and hormonal indicators during an oral glucose tolerance test (OGTT), Exp Clin Endocrinol 1987;vol. 80:91-96.

Ziegler, et al. Effects of hypercalcemia, hypercalcemia and calcitonin on glucose stimulated insulin secretion in man, Horm Metabol Res 1972;vol. 4:60.

Zolnierowicz, et al. Isolation, characterization, and chromosomal localization of the porcine calcitonin receptor gene, J Biol Chem 1994;vol. 269:19530-19538.

Poyner, et al. International union of pharmacology. XXXII. The mammalian calcitonin gene-related peptides, adrenomedullin, amylin, and calcitonin Receptors, Pharmacol Rev 2002;vol. 54:233-246.

Young, et al. Effects of plasma glucose and lactate, Adv Pharmacol 2005;vol. 52:193-208.

Yamin, et al. Cloning and characterization of a mouse brain calcitonin receptor complementary deoxyribonucleic acid and mapping of the calcitonin receptor gene, Endocrinology 1994;vol. 135:2635-2643.

Pittner, et al. Lack of effect of calcitonin gene-related peptide and amylin on major markers of glucose metabolism in hepatocytes, Eur J Pharmacol, 1997;vol. 325:189-197.

Fuente, et al. Nanoparticles as protein and gene carriers to mucosal surfaces, Nanomedicine, 2008;vol. 3:845-857.

Blahos, et al. The effect of calcitonin on glucose metabolism, Endokrinologie 1976;vol. 2:226-230.

Garcia-Fuentes, et al. New surface-modified lipid nanoparticles as delivery vehicles for salmon calcitonin, Int J Pharm 2005;296:122-132.

Gattereau, et al. Effect of acute and chronic administration of calcitonin on serum glucose in patients with paget's disease of bone, J Clin Endocrinol Metab 1980;vol. 51:354-357.

Giugliano, et al. Glucose metabolism in patients receiving chronic calcitonin treatment, 1982;vol. 8:213-216.

Giustina, et al. Synthetic salmon calcitonin is not diabetogenic in patients with normal or impaired glucose metabolism, J Endocrinol Invest 1985;vol. 8:19-23.

Heilker, et al. High content screening to monitor g protein-coupled receptor internalisation, Ernst Schering Foundation Symposium Proceedings, 2007;vol. 2:229-247; DOI 10.1007/2789_2006_011.

Lee, et al. Expression of the calcitonin receptor in bone marrow cell cultures and in bone: a specific marker of the differentiated osteoclast that is regulated by calcitoniin, Endocrinology 1995;vol. 136:4572-4581.

Mangiafico, et al. Effetti del trattamento associato short-term nifedipina-calcitonina sulla tolleranza al glucosio in ipertesi con metabolismo glicidico normale e alterrato, La Riforma Medica, 1958;vol. 103:563-566.

Nussenzveig, et al. Alternative splicing of a 48-nucleotide exon generates two isoforms of the human calcitonin receptor, Endocrinology 1995;vol. 136:2047-2051.

Passariello, et al. Calcitonin, a diabetogenic harmone? J Clin Endocrinol Metab 1981;vol. 53:318-323.

Petralito, et al. Effects of salmon calcitonin on blood glucose and insulin levels under basal conditions and after intravenous glucose load, J Endocrinol Invest 1979;vol. 2:209-211.

Gomez-Foix, et al. Anti-insulin effects of amylin and calcitonin-gene-related peptide on hepatic glycogen metabolism, Biochem J 1991;vol. 276:607-610.

Nishikawa, et al. A novel calcitonin receptor gene in human osteoclasts from normal bone marrow, FEBS Letters 1999;vol. 458:409-414.

Reid, et al. Effects of amylin and adrenomedullin on the skeleton, J Musculoskel Neuron Interact 2001;vol. 2:15-24.

Zolnierowicz, et al. Isolation, characterization, and chromosomal localization of the porcine calcitonin receptor gene, J Biol Chem 1994;vol. 259:19530-19538.

Young, et al. Diabetogenic effects of salmon calcitonin are attributable to amylin-like activity, Metabolism 1995;vol. 44:1581-1589.

Xiao, et al. High throughput screening for orphan and liganded GPCRs, Comb Chem High Throughput Screen 2008; vol. 11:195-215.

Waller, et al. Techniques: GPCR assembly, pharmacology and screening by flow cytometry, Trends Pharmacol Sci 2004;vol. 25:663-669.

Thomsen, et al. Functional assays for screening GPCR targets, Curr Opin Biotechnol 2005;vol. 16:655-665.

Takahashi, et al. Down regulation of calcitonin receptor mRNA expression by calcitonin during human osteoclast-like cell differentiation, J Clin Invest 1995;vol. 95:167-171.

Starke, et al. Effects of calcium and calcitonin on circulating levels of glucagon and glucose in diabetes mellitus, Diabetologia 1981; vol. 20:547-552.

Song, et al. Enhanced intestinal absorption of salmon calcitonin (sCT) from proliposomes containing bile salts, J Control Release 2005;vol. 106:298-308.

Smith, et al. Adrenomedullin: receptor and signal transduction, Biochem. Soc. Trans. 2002;vol. 30:432-437.

Sinko, et al. Biopharmaceutical approaches for developing and assesssing oral peptide delivery strategies and systems: in vitro permeability and in vivo oral absorption of salmon calcitonin, Pharm Res 1999;vol. 16;527-533.

Shen, et al. Intestinal patches for oral drug delivery, Pharm Res 2002;vol. 19:391-395.

Qi, et al. Identification of N-terminal receptor activity-modifying protein residues important for calcitonin gene-related peptide, adrenomedullin, and amylin receptor function, Mol Pharmacol 2008;vol. 74:1069-1071.

Purdue, et al. Molecular pharmacology of the calcitonin receptor, Receptor Channel 2002;vol. 8:243-255.

Prego, et al. J Control Release 2006;vol. 111:299-308.

Prego, et al. Efficacy and mechanism of action of chitosan nanocapsules for oral peptide delivery, Pharm Res 2006;vol. 23:549-556.

Prego, et al. Transmucosal macromolecular drug delivery, J Control Release 2005;vol. 101:151-162.

Notoya, et al. A novel member of the calcitonin gene-related peptide family, calcitonin receptor-stimulating peptide, inhibits the formation and activity of osteoclasts, Eur J Pharmacol 2007;vol. 560:234-239.

Mansoor, et al. Oral delivery of mono-PEGylated sCT (Lys18) in rats: regional difference in stability and hypocalcemic effect, Pharm Dev Technol 2005;vol. 10:389-396.

Lin, et al. Expression cloning of an adenylate cyclase-coupled calcitonin receptor, Science 1991;vol. 254:1022-1024.

Leifert, et al. G-protein-coupled receptors in drug discovery: nanosizing using cell-free technologies and molecular biology approaches, J Biomol Screen 2005;vol. 10:765-779.

Kuestner, et al. Cloning and characterization of an abundant subtype of the human calcitonin receptor, Mol Pharmacol 1994;vol. 46:246-255.

(56) References Cited

OTHER PUBLICATIONS

Kostenis, E. G proteins in drug screening: from analysis of receptor-G protein specificity to manipulation of GPCR-mediated signalling pathways, Curr Pharm Design 2006;12:1703-1715.
Jonderko, K. Effect of calcitonin on gastric emptying in patients with an active duodenal ulcer, Gut 1989;30:430-435.
Jacoby, et al. The 7TM G-protein-coupled receptor target family, ChemMedChem 2006;vol. 1:760-782.
Heilker, et al. Confocal fluorescence microscopy for high-throughput screening of G-protein coupled receptors, Curr Med Chem 2005;vol. 12:2551-2559.
Hay, et al. CGRP receptor heterogeneity: a role for receptor component protein? Trends Endocrin Met 2003; vol. 14:3-4.
Hay, et al. Desensitisation of adrenomedullin and CGRP receptors, Regul Peptides 2003;vol. 112:139-145.
Hay, et al. Determinants of 1-piperidinecarboxamide, N-[2-[[5-amino-1-[[4-(4-pyridinyl)-1-piperazinyl]carbonyl]pentyl] amino]-1-[(3,5-dibromo-4-hydroxyphenyl)methyl]-2-oxoethyl]-4-(1,4-dihydro-2-oxo-3(2H)-quinazolinyl) (BIBN4096BS) affinity for calcitonin gene-related peptide and amylin receptors-the role of receptor activity modifying protein 1, Mol Pharmacol 2006;vol. 70:1984-1991.
Hay, et al. Pharmacological discrimination of calcitonin receptor: receptor activity-modifying protein complexes, Mol Pharmacol 2005; vol. 67:1655-1665.
Hay, et al. CL/RAMP2 and CL/RAMP3 produce pharmacologically distinct adrenomedullin receptors: a comparison of effects of adrenomedullin22-52, CGRP8-37 and BIBN4096BS, Br J Pharmacol 2003;vol. 140:477-486.
Hay, et al. A comparison of the actions of BIBN4096BS and CGRP8±37 on CGRP and adrenomedullin receptors expressed on Sk-N-Mc, L6, col. 29 and Rat 2 cells, Br J Pharmacol 2002;vol. 137:80-86.
Yang et al., "Synthesis of Salmon Calcitonin Analogs Using F-moc based Chemistry on MBHA Resins", Chinese Chemical Letters, vol. 10, No. 7, pp. 549-552 (1999).
Twery et al., "Analogue separates biological effects of salmon calcitonin on brain and renal cortical membranes", European Journal of Pharmacology, 155, (1988), pp. 285-292.
Lutz et al., "Amylin receptors mediate the anoretic action of salmon calcitonin", Peptides, 21 (2000), pp. 233-238.
Twery et al., "Neuronal membrane sensitivity to a salmon calcitonin analogue with negligible ability to lower serum calcium", Neuroscience Letters, 86 (1988), pp. 82-88.
Aronne et al., "Progressive reduction in Body Weight after Treatment with the Amylin Analog Pramlintide in Obese Subjects: A Phase 2, Randomized, Placebo-Controlled, Dose-Escalation Study", The Journal of Clinical Endocrinology & Metabolism, 92(8) 2007, pp. 2977-2983.
Prete et al., "Effects of amylin and salmon calcitonin on feeding and drinking behavior in pygmy goats", Physiology & Behavior, 75 (2002), pp. 593-599.
Reidelberger et al., "Effects of amylin-related peptides on food intake, meal patterns, and gastric emptying in rats", Am J Physiol Regulatory Integrative Comp Physiol, 282 (2002), pp. R1395-R1404.
Chelikani et al., "Intravenous Infusion of Peptide YY(3-36) Potently Inhibits Food Intake in Rats", Endocrinology, 146 (2), pp. 879-888 (2005).
Hallschmid et al., "Manipulating central nervous mechanisms of food intake and body weight regulation by intranasal administration of neuropeptides in man", Physiology & Behavior, 83 (2004), pp. 55-64.
Tavares et al., "N-Procalcitonin: Central Effects on Feeding and Energy Homeostasis in Rats", Endocrinology, 148(4), pp. 1891-1901 (2007).
Eiden et al., "Salmon calcitonin—a potent inhibitor of food intake in states of impaired leptin signaling in laboratory rodents", Journal of Physiology, (2002), 541.3, pp. 1041-1048.
Wielinga et al., "The acute effect of amylin and salmon calcitonin on energy expenditure", Physiology & Behavior, 91 (2007) pp. 212-217.
Chelikani et al., "Effects of Intermittent Intraperitoneal Infusion of Salmon Calcitonin on Food Intake and Adiposity in Obese Rats", Articles in Press., Am J Physiol Regul Integ Comp Physiol, (Aug. 29, 2007), pp. 1-41.
Bello et al., "Salmon calcitonin reduces food intake through changes in meal sizes in male rhesus monkeys", Articles in Press. Am J Physiol Regul Integr Comp Physiol, (May 14, 2008), pp. 1-25.
Chelikani et al., "Intravenous infusion of glucagon-like peptide-1 potently inhibits food intake, sham feeding, and gastric emptying rats", Articles in PresS. Am J Physiol Regul Integr Comp Physiol, (Feb. 17, 2005) 50 ps.
Perlow et al., "Calcitonin Reduces Feeding in Man, Monkey and Rat", Pharmacology & Behavior, vol. 12, pp. 609-612 (Feb. 1979).
Ray et al., "Production of Recombinant Salmon Calcitonin by In Vitro Amidation of an *Escherichia coli* Produced Precursor Peptide", Biotechnology, vol. 11, (Jan. 1993), pp. 64-70.
Ray et al., "Production of salmon calcitonin by direct expression of a glycine-extended precursor in *Escherichia coli*", Protein Expression and Purification, 26, pp. 249-259 (2002).
Mehta et al., "Oral Delivery and Recombinant Production of Peptide Hormones, Part II: Recombinant Production of Therapeutic Peptides", Biopharm. International, (Jul. 2004), pp. 44-46.
Mack et al., "Davalintide (AC2307), a novel amylin-mimetic peptide: enhanced pharmacological properties over native amylin to reduce food intake and body weight", International Journal of Obesity (2009), pp. 1-11.
Prigge et al., "New insights into copper monooxygenases and peptide amidation: structure, mechanism and function", CMLS, Cell. Mol. Life Sci., vol. 57, Aug. 2000, pp. 1236-1259.
Shimizu et al., "Enhancement of Antimicrobial Activity of Neuropeptide Y by N-Terminal Truncation", Antimicrobial Agents and Chemotherapy, vol. 42, No. 10, Oct. 1998, pp. 2745-2746.
Zarandi et al., "Synthesis and biological activities of highly potent antagonists of growth hormone-releasing hormone", Proc. Natl. Acad. Sci. USA, vol. 91, Dec. 1997, pp. 12298-12302.
Dasgupta et al., "N-Terminal Acylation of Somatostatin Analog with Long Chain Fatty Acids Enhances Its Stability and Anti-Proliferative Activity in Human Breast Adenocarcinoma Cells", Biol. Pharm. Bull. 25(1) Jan. 2002, pp. 29-36.
Brinkmeier et al., "An endogenous pentapeptide acting as a sodium channel blocker in inflammatory autoimmune disorders of the central nervous system", Nature Medicine, vol. 6, No. 7, Jul. 2000, pp. 808-811.
Gaudreau et al., Affinity of Human Growth Hormone-Releasing Factor (1-29) NH2 Analogues for GRF Binding Sites in Rat Adenopituitary, Journal of Medical Chemistry, May 1992, vol. 35, No. 10, pp. 1864-1869.
John et al., "N-Terminal Acetylations Protects Glucagon-Like Peptide GLP-1-(7-34)-Amide from DPP-IV-Mediated Degradation Retaining CAMP- and Insulin-Releasing Capacity", European Journal of Medical Research, Feb. 25, 20008, 13, pp. 73-78.
Deakin et al., "Influence of N-terminal acetylation and C-terminal proteolysis on the analgesic activity of β-endorphin", Biochem. J., Sep. 1, 1980, vol. 189, Part 3, pp. 501-506.
International Search Report and Written Opinion from International Application No. PCT/US2012/063332 dated Apr. 1, 2013.

\* cited by examiner

Figures 12A (top) and 12B (bottom)

Figures 13A (top) and 13B (bottom)

Figures 14A (top) and 14B (bottom)

Figures 15A (top) and 15B (bottom)

Figures 16A (top) and 16B (bottom)

Figures 17A (top) and 17B (bottom)

PEPTIDE ANALOGS FOR TREATING DISEASES AND DISORDERS

RELATED APPLICATIONS

This application claims the benefit of and priority to U.S. Provisional Application Ser. No. 61/554,771, filed Nov. 2, 2011, and U.S. Provisional Application Ser. No. 61/578,620, filed Dec. 21, 2011, the entirety of these applications are hereby incorporated herein by reference.

FIELD

The embodiments disclosed herein relate to mimetics of calcitonin, and more particularly to their use in the treatment of various diseases and disorders, including, but not limited to diabetes (Type I and Type II), excess bodyweight, excessive food consumption and metabolic syndrome, the regulation of blood glucose levels, the regulation of response to glucose tolerance tests, the regulation of food intake, the treatment of osteoporosis and the treatment of osteoarthritis.

BACKGROUND

Worldwide, there are about 250 million diabetics and the number is projected to double in the next two decades. Over 90% of this population suffers from type 2 diabetes mellitus (T2DM). It is estimated that only 50-60% of persons affected with T2DM or in stages preceding overt T2DM are currently diagnosed.

T2DM is a heterogeneous disease characterized by abnormalities in carbohydrate and fat metabolism. The causes of T2DM are multi-factorial and include both genetic and environmental elements that affect β-cell function and insulin sensitivity in tissues such as muscle, liver, pancreas and adipose tissue. As a consequence impaired insulin secretion is observed and paralleled by a progressive decline in β-cell function and chronic insulin resistance. The inability of the endocrine pancreas to compensate for peripheral insulin resistance leads to hyperglycaemia and onset of clinical diabetes. Tissue resistance to insulin-mediated glucose uptake is now recognized as a major pathophysiologic determinant of T2DM.

A success criterion for an optimal T2DM intervention is the lowering of blood glucose levels, which can be both chronic lowering of blood glucose levels and increased ability to tolerate high glucose levels after food intake, described by lower peak glucose levels and faster clearance. Both of these situations exert less strain on β-cell insulin output and function.

Type I diabetes is characterised by a loss of the ability to produce insulin in response to food intake and hence an inability to regulate blood glucose to a normal physiological level.

The physical structure of bone may be compromised by a variety of factors, including disease and injury. One of the most common bone diseases is osteoporosis, which is characterized by low bone mass and structural deterioration of bone tissue, leading to bone fragility and an increased susceptibility to fractures, particularly of the hip, spine and wrist. Osteoporosis develops when there is an imbalance such that the rate of bone resorption exceeds the rate of bone formation. Administering an effective amount of an anti-resorptive agent, such as calcitonin, has shown to prevent resorption of bone.

Inflammatory or degenerative diseases, including diseases of the joints, e.g. osteoarthritis (OA), rheumatoid arthritis (RA) or juvenile rheumatoid arthritis (JRA), and including inflammation that results from autoimmune response, e.g. lupus, ankylosing spondylitis (AS) or multiple sclerosis (MS), can lead to substantial loss of mobility due to pain and joint destruction. Cartilage that covers and cushions bone within joints may become degraded over time thus undesirably permitting direct contact of two bones that can limit motion of one bone relative to the other and/or cause damage to one by the other during motion of the joint. Subchondral bone just beneath the cartilage may also degrade. Administering an effective amount of an anti-resorptive agent, such as calcitonin, may prevent resorption of bone.

SUMMARY

Calcitonin mimetics are disclosed herein.

According to aspects illustrated herein, there is disclosed a method that includes administering to a patient an effective amount of a peptide selected from the group consisting of: SEQ ID NO:11, SEQ ID NO:12, SEQ ID NO:13, SEQ ID NO:14, SEQ ID NO:15, and SEQ ID NO:17 to effect a weight reduction in the patient.

According to aspects illustrated herein, there is disclosed a method that includes administering to a patient an effective amount of a peptide selected from the group consisting of: SEQ ID NO:11, SEQ ID NO:12, SEQ ID NO:13, SEQ ID NO:14, SEQ ID NO:15, and SEQ ID NO:17 to effect postprandial glycemic control in the patient.

According to aspects illustrated herein, there is disclosed a method that includes administering to a patient an effective amount of a peptide selected from the group consisting of: SEQ ID NO:11, SEQ ID NO:12, SEQ ID NO:13, SEQ ID NO:14, SEQ ID NO:15, and SEQ ID NO:17 to effect an improvement in glycemic control in the patient.

According to aspects illustrated herein, there is disclosed a method that includes administering to a patient an effective amount of a peptide selected from the group consisting of: SEQ ID NO:11, SEQ ID NO:12, SEQ ID NO:13, SEQ ID NO:14, SEQ ID NO:15, and SEQ ID NO:17 to affect an improvement in glycemic control in the patient.

According to aspects illustrated herein, there is disclosed a method that includes administering to a patient an effective amount of a peptide of SEQ ID NO:18 having the sequence $C_m$SNLSTCVLGKLSQELHKLQTYPRTDVGANXaaXaa$_a$ so as to reduce at least one of bone resorption and cartilage degradation in the patient.

BRIEF DESCRIPTION OF THE DRAWINGS

The presently disclosed embodiments will be further explained with reference to the attached drawings, which illustrate the principles of the presently disclosed embodiments.

Figure 1A:
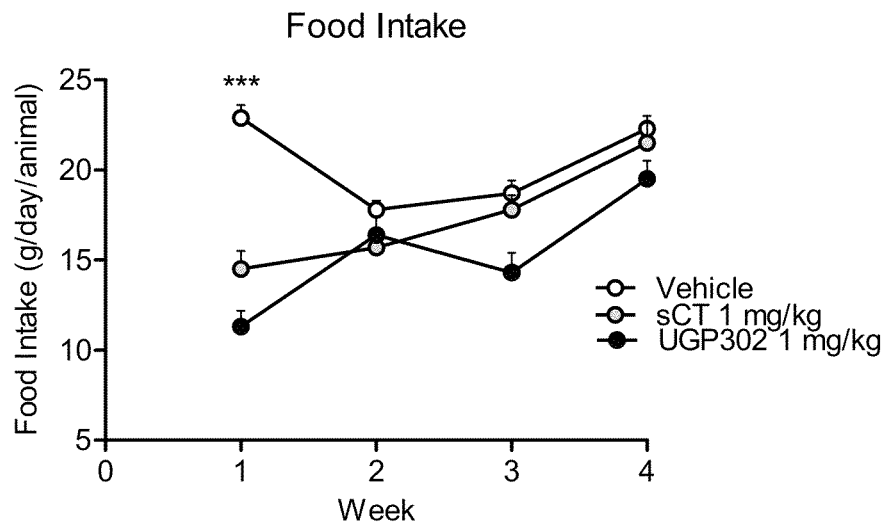
FIGS. 1A-D show the effect of chronic oral salmon calcitonin ("sCT") versus oral UGP 302 administration on body weight and food intake in DIO rats as measured in Example 1.
Figure 1B:
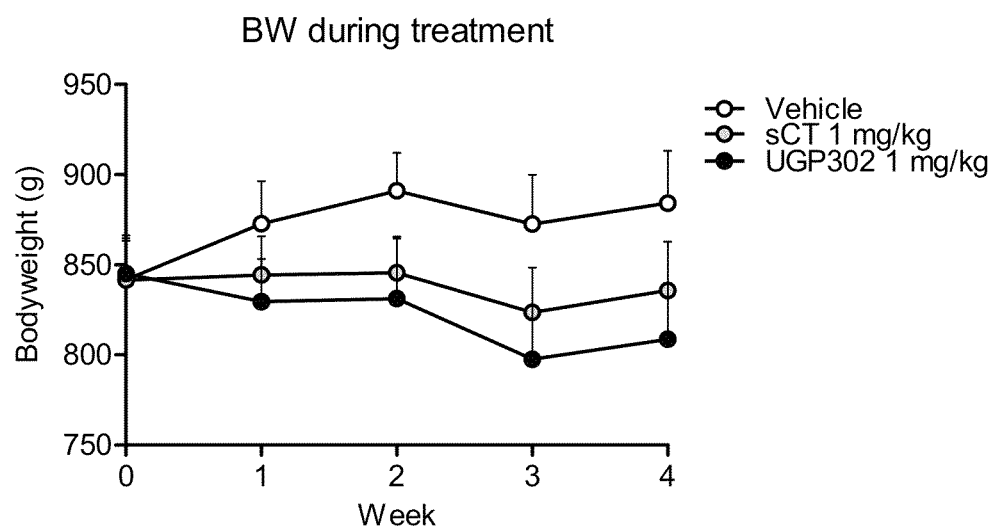
Figure 1C:
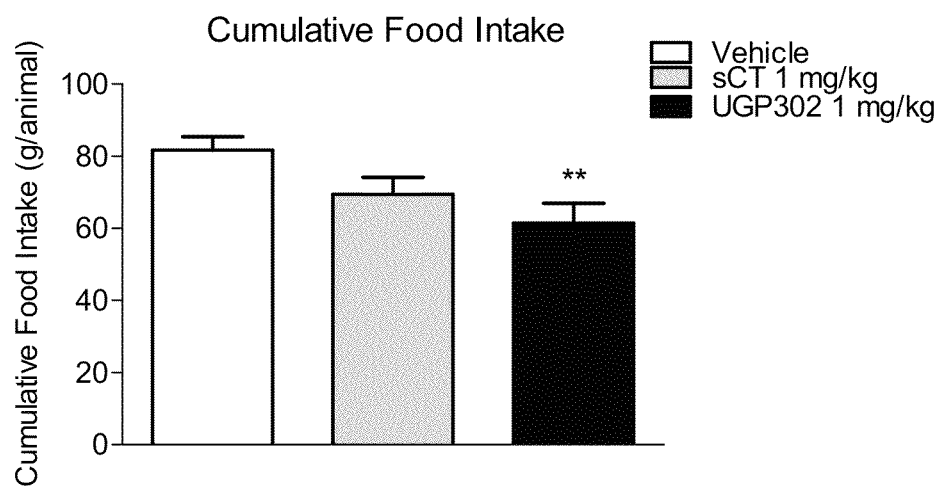
Figure 1D:
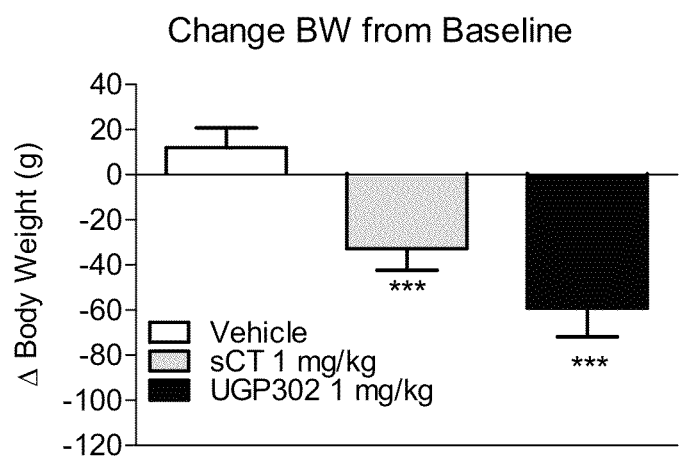

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Calcitonins are highly conserved over a wide range of species. Full-length native calcitonin is 32 amino acids in length. The sequences of examples of calcitonins are set out below:

| Salmon | CSNLSTCVLGKLSQELHKL QTYPRTNTGSGTP | SEQ ID NO: 1 |
|---|---|---|
| Mouse | CGNLSTCMLGTYTQDLNKF HTFPQTSIGVEAP | SEQ ID NO: 2 |
| Chicken | CASLSTCVLGKLSQELHKL QTYPRTDVGAGTP | SEQ ID NO: 3 |
| Eel | CSNLSTCVLGKLSQELHKL QTYPRTDVGAGTP | SEQ ID NO: 4 |
| Rat | CGNLSTCMLGTYTQDLNKF HTFPQTSIGVGAP | SEQ ID NO: 5 |
| Horse | CSNLSTCVLGTYTQDLNKF HTFPQTAIGVGAP | SEQ ID NO: 6 |
| Canine-1 | CSNLSTCVLGTYSKDLNNF HTFSGIGFGAETP | SEQ ID NO: 7 |
| Canine-2 | CSNLSTCVLGTYTQDLNKF HTFPQTAIGVGAP | SEQ ID NO: 8 |
| Porcine | CSNLSTCVLSAYWRNLNNF HRFSGMGFGPETP | SEQ ID NO: 9 |
| Human | CGNLSTCMLGTYTQDFNKF HTFPQTAIGVGAP | SEQ ID NO: 10 |

Embodiments of the present disclosure relate to calcitonin mimetics. The amino acid sequence of the calcitonin mimetics of the present disclosure are found in Table 1 below.

TABLE 1

| Calcitonin Mimetic ("CM") | Amino Acid Sequence | SEQ ID NO: |
|---|---|---|
| UGP281 | AcCSNLSTCVLG KLSQELHKLQT YPRTDVGANTY-NH$_2$ | 11 |
| UGP283 | AcCSNLSTCVLG RLSQELHRLQTF PRTDVGANTAcY | 12 |
| UGP284 | PrCSNLSTCVLGKL SQELHKLQTY PRTNTGSGTP-NH$_2$ | 13 |
| UGP298 | SuccCSNLSTCVLG KLSQELHKLQTY PRTNTGSGTP-NH$_2$ | 14 |
| UGP302 | AcCSNLSTCVLG KLSQELHKLQTY PRTDVGANAP-NH$_2$ | 15 |
| UGP303 | KCSNLSTCVL GKLSQELHKLQTY PRTDVGANTY-NH$_2$ | 16 |
| UGP306 | SuccCSNLSTCVL GKLSQELHKLQTY PRTDVGANAY-NH$_2$ | 17 |
| UGP1000 | C$_m$SNLSTCVLG KLSQELHKLQTYPR TDVGANXaaXaa$_a$ | 18 |

In some embodiments, the cysteine at position 1 of the calcitonin mimetics discussed supra is modified ("C$_m$") to reduce the positive charge of the first amino acid. For example, an acetyl group (SEQ ID NOs: 11, 12 and 15), propionyl group (SEQ ID NO: 13), or succinyl group (SEQ ID NOs: 14 and 17) may be substituted on cysteine-1. In some embodiments, the amino acid at the last position ("Xaa$_a$") (position 32 in SEQ ID Nos: 11, 13-15 and 17-18 or position 33 in SEQ ID NO: 16) may include an amidated group "NH$_2$". Alternative ways of reducing positive charge include, but are not limited to, polyethylene glycol-based PEGylation, or the addition of another amino acid such as glutamic acid or aspartic acid at the N-terminus. Alternatively, other amino acids may be added to the N-terminus of peptides discussed supra including, but not limited to, lysine, glycine, formylglycine, leucine, alanine, acetyl alanine, and dialanyl. An example of an amino acid added to the N-terminus of peptides includes SEQ ID NO:16, where a lysine has been added.

"Xaa" in SEQ ID NO: 18 in Table 1 can be any naturally occurring amino acid. In an embodiment Xaa at position 31 is selected from one of threonine or alanine. In an embodiment Xaa at position 32 is selected from one of tyrosine or proline. Thus, SEQ ID NOs: 11, 15, 16 and 17, are encompassed by SEQ ID NO: 18.

As those of skill in the art will appreciate, peptides having a plurality of cysteine residues frequently form a disulfide bridge between two such cysteine residues. All such peptides set forth herein are defined as optionally including one or more such disulfide bridges. While calcitonin mimetics of the present disclosure may exist in free acid form, it is preferred that the C-terminal amino acid be amidated. Applicants expect that such amidation may contribute to the effectiveness and/or bioavailability of the peptide. A preferred technique for manufacturing amidated versions of the calcitonin mimetics of the present disclosure is to react precursors (having glycine in place of the C-terminal amino group of the desired amidated product) in the presence of peptidylglycine alpha-amidating monooxygenase in accordance with known techniques wherein the precursors are converted to amidated products in reactions described, for example, in U.S. Pat. No. 4,708,934 and European Patent Publication Nos. 0 308 067 and 0 382 403. Recombinant production is preferred for both the precursor and the enzyme that catalyzes the conversion of the precursor to salmon calcitonin. Such recombinant production is discussed in Biotechnology, Vol. 11 (1993) pp. 64-70, which further describes a conversion of a precursor to an amidated product. The recombinant product reported there is identical to natural salmon calcitonin, and to salmon calcitonin produced using solution and solid phase chemical peptide synthesis. Production of amidated products may also be accomplished using the process and amidating enzyme set forth by Consalvo, et al in U.S. Pat. No. 7,445,911; Miller et al, U.S. Patent Publication No. 2006/0292672; Ray et al, 2002, Protein Expression and Purification, 26:249-259; and Mehta, 2004, Biopharm. International, July, pp. 44-46.

The production of the preferred amidated peptides may proceed, for example, by producing glycine-extended precursor in *E. coli* as a soluble fusion protein with glutathione-S-transferase, or by direct expression of the precursor in accordance with the technique described in U.S. Pat. No. 6,103,495. Such a glycine extended precursor has a molecular structure that is identical to the desired amidated product except at the C-terminus (where the product terminates —X—NH$_2$, while the precursor terminates —X-gly, X being the C-terminal amino acid residue of the product). An alpha-amidating enzyme described in the publications above catalyzes conversion of precursors to product. That enzyme is preferably recombinantly produced, for example, in Chinese Hamster Ovary (CHO) cells), as described in the Biotechnology and Biopharm. articles cited above.

Free acid forms of peptide active agents of the present disclosure may be produced in like manner, except without including a C-terminal glycine on the "precursor", which precursor is instead the final peptide product and does not require the amidation step.

Except where otherwise stated, the preferred dosage of the calcitonin mimetics of the present disclosure is identical for both therapeutic and prophylactic purposes. Desired dosages are discussed in more detail, infra, and differ depending on mode of administration.

Except where otherwise noted or where apparent from context, dosages herein refer to weight of active compounds unaffected by pharmaceutical excipients, diluents, carriers or other ingredients, although such additional ingredients are desirably included, as shown in the examples herein. Any dosage form (capsule, tablet, injection or the like) commonly used in the pharmaceutical industry for delivery of peptide active agents is appropriate for use herein, and the terms "excipient", "diluent", or "carrier" includes such non-active ingredients as are typically included, together with active ingredients in such dosage form in the industry. A preferred oral dosage form is discussed in more detail, infra, but is not to be considered the exclusive mode of administering the active agents of the present disclosure.

The calcitonin mimetics of the present disclosure can be administered to a patient to treat a number of diseases or disorders. As used herein, the term "patient" means any organism belonging to the kingdom Animalia. In an embodiment, the term "patient" refers to vertebrates, more preferably, mammals including humans.

Accordingly, the present disclosure provides a method of treatment of type I diabetes, Type II diabetes or metabolic syndrome, obesity, or of appetite suppression, or for mitigating insulin resistance, or for reducing an undesirably high fasting serum glucose level, or for reducing an undesirably high peak serum glucose level, or for reducing an undesirably high peak serum insulin level, or for reducing an undesirably large response to a glucose tolerance test, or for treating osteoporosis, or for treating osteoarthritis.

As used herein, the term "glycemic control" refers to the typical levels of blood sugar (glucose) in a person with diabetes mellitus. The percentage of hemoglobin which is glycosolated (measured as hemoglobin A1c) is used as a proxy measure of long-term glycemic control. As used herein, the term "improved glycemic control" refers to the ability of a calcitonin mimetic of the present disclosure to reduce the percentage of hemoglobin which is glycosolated.

There are a number of art-recognized measures of normal range for body weight in view of a number of factors such as gender, age and height. A patient in need of treatment or prevention regimens set forth herein include patients whose body weight exceeds recognized norms or who, due to heredity, environmental factors or other recognized risk factor, are at higher risk than the general population of becoming overweight or obese. In accordance with the present disclosure, it is contemplated that the calcitonin mimetics may be used to treat diabetes where weight control is an aspect of the treatment.

In an embodiment, the method includes enteral administration to a patient in need thereof for treatment of a said condition of a pharmaceutically effective amount of any one of the peptides described herein.

In an embodiment, the method includes parenteral administration to a patient in need thereof for treatment of a said condition of a pharmaceutically effective amount of any one of the peptides described herein. For parenteral administration (including intraperitoneal, subcutaneous, intravenous, intradermal or intramuscular injection), solutions of a peptide of the present disclosure in either sesame or peanut oil or in aqueous propylene glycol may be employed, for example. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Peptides may be formulated in sterile form in multiple or single dose formats such as being dispersed in a fluid carrier such as sterile physiological saline or 5% saline dextrose solutions commonly used with injectables.

Said method may include a preliminary step of determining whether the patient suffers from a said condition, and/or a subsequent step of determining to what extent said treatment is effective in mitigating the condition in said patient, e.g. in each case, carrying out an oral glucose tolerance test or a resting blood sugar level.

For improved control over the weight of the patient, to produce a loss of weight or an avoidance of weight gain, the active compound is preferably administered at least twice per day, e.g. from 2-4 times per day. Formulations of the active compound may contain a unit dosage appropriate for such an administration schedule. The active compounds may be administered with a view to controlling the weight of a patient undergoing treatment for diabetes or metabolic syndrome.

Oral enteral formulations are for ingestion by swallowing for subsequent release in the intestine below the stomach, and hence delivery via the portal vein to the liver, as opposed to formulations to be held in the mouth to allow transfer to the bloodstream via the sublingual or buccal routes.

Suitable dosage forms for use in the present disclosure include tablets, mini-tablets, capsules, granules, pellets, powders, effervescent solids and chewable solid formulations. Such formulations may include gelatin which is preferably hydrolysed gelatin or low molecular weight gelatin. Such formulations may be obtainable by freeze drying a homogeneous aqueous solution comprising calcitonin or a fragment or conjugate thereof and hydrolysed gelatin or low molecular weight gelatin and further processing the resulting solid material into said oral pharmaceutical formulation, and wherein the gelatin may have a mean molecular weight from 1000 to 15000 Daltons. Such formulations may include a protective carrier compound such as 5-CNAC or others as disclosed herein.

Whilst oral formulations such as tablets and capsules are preferred, compositions for use in the present disclosure may take the form of syrups, elixirs or the like and suppositories or the like. Oral delivery is generally the delivery route of choice since it is convenient, relatively easy and generally painless, resulting in greater patient compliance relative to other modes of delivery. However, biological, chemical and physical barriers such as varying pH in the gastrointestinal tract, powerful digestive enzymes, and active agent impermeable gastrointestinal membranes, makes oral delivery of calcitonin like peptides to mammals problematic, e.g. the oral delivery of calcitonins, which are long-chain polypeptide hormones secreted by the parafollicular cells of the thyroid gland in mammals and by the ultimobranchial gland of birds and fish, originally proved difficult due, at least in part, to the insufficient stability of calcitonin in the gastrointestinal tract as well as the inability of calcitonin to be readily transported through the intestinal walls into the blood stream.

Suitable oral formulations are however described below.

Treatment of Patients

In an embodiment, a calcitonin mimetic of the present disclosure is administered at adequate dosage to maintain serum levels of the mimetic in patients between 5 and 500 picograms per milliliter, preferably between 10 and 250 picograms per milliliter. The serum levels may be measured by radioimmunoassay techniques known in the art. The attending physician may monitor patient response, and may then alter the dosage somewhat to account for individual patient metabolism and response. Near simultaneous release is best achieved by administering all components of the present disclosure as a single pill or capsule. However, the disclosure also includes, for example, dividing the required amount of the calcitonin mimetic among two or more tablets or capsules which may be administered together such that they together provide the necessary amount of all ingredients. "Pharmaceutical composition," as used herein includes but is not limited to a complete dosage appropriate to a particular administration to a patient regardless of whether one or more tablets or capsules (or other dosage forms) are recommended at a given administration.

A calcitonin mimetic of the present disclosure may be formulated for oral administration using the methods employed in the Unigene Enteripep® products. These may include the methods as described in U.S. Pat. No. 5,912,014, U.S. Pat. No. 6,086,918, U.S. Pat. No. 6,673,574, U.S. Pat. No. 7,316,819, U.S. Pat. No. 8,093,207, and US Publication No. 2009/0317462. In particular, it may include the use of conjugation of the compound to a membrane translocator such as the protein transduction domain of the HIV TAT protein, co-formulation with one or more protease inhibitors, and/or a pH lowering agent which may be coated and/or an acid resistant protective vehicle and/or an absorption enhancer which may be a surfactant.

In an embodiment, a calcitonin mimetic of the present disclosure is preferably formulated for oral delivery in a manner known in U.S. Patent Publication No. 2009/0317462. One preferred oral dosage form in accordance with the present disclosure is set forth in Table 2 below:

TABLE 2

| ACTIVE AGENT OR EXCIPIENT | FUNCTION |
|---|---|
| A Calcitonin Mimetic selected from one of SEQ ID NO: 11-SEQ ID NO: 18 | Active agent |
| Coated Citric Acid Particles | Protease Inhibitor |
| Lauroylcarnitine | Absorption Enhancer |
| Nonionic Polymer | Subcoat |
| Eudragit L30D-55 | Enteric Coat |

In an embodiment, a calcitonin mimetic of the present disclosure may be formulated for enteral, especially oral, administration by admixture with a suitable carrier compound. Suitable carrier compounds include those described in U.S. Pat. No. 5,773,647 and U.S. Pat. No. 5,866,536 and amongst these, 5-CNAC (N-(5-chlorosalicyloyl)-8-aminocaprylic acid, commonly as its disodium salt) is particularly effective. Other preferred carriers or delivery agents are SNAD (sodium salt of 10-(2-Hydroxybenzamido)decanoic acid) and SNAC (sodium salt of N-(8-[2-hydroxybenzoyl] amino)caprylic acid). In an embodiment, a pharmaceutical composition of the present disclosure comprises a delivery effective amount of carrier such as 5-CNAC, i.e. an amount sufficient to deliver the compound for the desired effect. Generally, the carrier such as 5-CNAC is present in an amount of 2.5% to 99.4% by weight, more preferably 25% to 50% by weight of the total composition.

In addition, WO 00/059863 discloses the disodium salts of formula I

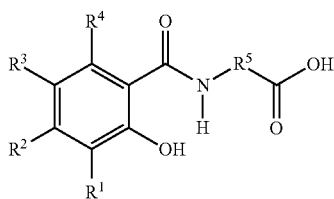

wherein $R^1$, $R^2$, $R^3$, and $R^4$ are independently hydrogen, —OH, —NR$^6$R$^7$, halogen, $C_1$-$C_4$ alkyl, or $C_1$-$C_4$ alkoxy; $R^5$ is a substituted or unsubstituted $C_2$-$C_{16}$ alkylene, substituted or unsubstituted $C_2$-$C_{16}$ alkenylene, substituted or unsubstituted $C_1$-$C_{12}$ alkyl(arylene), or substituted or unsubstituted aryl ($C_1$-$C_{12}$ alkylene); and $R^6$ and $R^7$ are independently hydrogen, oxygen, or $C_1$-$C_4$ alkyl; and hydrates and solvates thereof as particularly efficacious for the oral delivery of active agents, such as calcitonins, e.g. salmon calcitonin, and these may be used in the present disclosure.

Preferred enteric formulations using optionally micronised 5-CNAC may be generally as described in WO2005/014031.

The compound may be formulated for oral administration using the methods employed in the Capsitonin product of Bone Medical Limited. These may include the methods incorporated in Axcess formulations. More particularly, the active ingredient may be encapsulated in an enteric capsule capable of withstanding transit through the stomach. This may contain the active compound together with a hydrophilic aromatic alcohol absorption enhancer, for instance as described in WO02/028436. In a known manner the enteric coating may become permeable in a pH sensitive manner, e.g. at a pH of from 3 to 7. WO2004/091584 also describes suitable formulation methods using aromatic alcohol absorption enhancers.

The compound may be formulated using the methods seen in the Oramed products, which may include formulation with omega-3 fatty acid as seen in WO2007/029238 or as described in U.S. Pat. No. 5,102,666.

Generally, the pharmaceutically acceptable salts (especially mono or di sodium salts), solvates (e.g. alcohol solvates) and hydrates of these carriers or delivery agents may be used.

Oral administration of the pharmaceutical compositions according to the disclosure can be accomplished regularly, e.g. once or more on a daily or weekly basis; intermittently, e.g. irregularly during a day or week; or cyclically, e.g. regularly for a period of days or weeks followed by a period without administration. The dosage form of the pharmaceutical compositions of the presently disclosed embodiments can be any known form, e.g. liquid or solid dosage forms. The liquid dosage forms include solution emulsions, suspensions, syrups and elixirs. In addition to the active compound and carrier such as 5-CNAC, the liquid formulations may also include inert excipients commonly used in the art such as, solubilizing agents e.g. ethanol; oils such as cottonseed, castor and sesame oils; wetting agents; emulsifying agents; suspending agents; sweeteners; flavourings; and solvents such as water. The solid dosage forms include capsules, soft-gel capsules, tablets, caplets, powders, granules or other solid oral dosage forms, all of which can be prepared by methods well known in the art. The pharmaceutical compositions may additionally comprise additives in amounts customarily employed including, but not limited to, a pH adjuster, a preservative, a flavorant, a taste-masking agent, a fragrance, a humectant, a tonicifier, a colorant, a surfactant, a plasticizer, a lubricant such as magnesium stearate, a flow aid, a compression aid, a solubilizer, an excipient, a diluent such as microcrystalline cellulose, e.g. Avicel PH 102 supplied by FMC corporation, or any combination thereof. Other additives may include phosphate buffer salts, citric acid, glycols, and other dispersing agents. The composition may also include one or more enzyme inhibitors, such as actinonin or epiactinonin and derivatives thereof; aprotinin, Trasylol and Bowman-Birk inhibitor. Further, a transport inhibitor, i.e. a [rho]-glycoprotein such as Ketoprofin, may be present in the compositions of the present disclosure. The solid pharmaceutical compositions of the instant disclosure can be prepared by conventional methods e.g. by blending a mixture of the active compound, the carrier such as 5-CNAC, and any other ingredients, kneading, and filling into capsules or, instead of filling into capsules, molding followed by further tableting or compression-molding to give tablets. In addition, a solid dispersion may be formed by known methods followed by further processing to form a tablet or capsule. Preferably, the ingredients in the pharmaceutical compositions of the instant disclosure are homogeneously or uniformly mixed throughout the solid dosage form.

Alternatively, the active compound may be formulated as a conjugate with said carrier, which may be an oligomer as described in US2003/0069170, e.g.

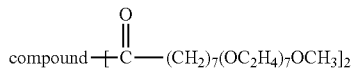

Such conjugates may be administered in combination with a fatty acid and a bile salt as described there.

Conjugates with polyethylene glycol (PEG) may be used, as described for instance in Mansoor et al.

Alternatively, active compounds may be admixed with nitroso-N-acetyl-D,L-penicillamine (SNAP) and Carbopol solution or with taurocholate and Carbapol solution to form a mucoadhesive emulsion.

The active compound may be formulated by loading into chitosan nanocapsules as disclosed in Prego et al (optionally PEG modified as in Prego Prego C, Torres D, Fernandez-Megia E, Novoa-Carballal R, Quiñoá E, Alonso M J.) or chitosan or PEG coated lipid nanoparticles as disclosed in Garcia-Fuentes et al. Chitosan nanoparticles for this purpose may be iminothiolane modified as described in Guggi et al. They may be formulated in water/oil/water emulsions as described in Dogru et al. The bioavailability of active compounds may be increased by the use of taurodeoxycholate or lauroyl carnitine as described in Sinko et al or in Song et al. Generally, suitable nanoparticles as carriers are discussed in de la Fuente et al and may be used in the present disclosure.

Other suitable strategies for oral formulation include the use of a transient permeability enhancer (TPE) system as described in WO2005/094785 of Chiasma Ltd. TPE makes use of an oily suspension of solid hydrophilic particles in a hydrophobic medium to protect the drug molecule from inactivation by the hostile gastrointestinal (GI) environment and at the same time acts on the GI wall to induce permeation of its cargo drug molecules.

Further included is the use of glutathione or compounds containing numerous thiol groups as described in US2008/0200563 to inhibit the action of efflux pumps on the mucous membrane. Practical examples of such techniques are described also in Caliceti, P. Salmaso, S., Walker, G. and Bernkop-Schnürch, A. (2004) 'Development and in vivo evaluation of an oral insulin-PEG delivery system.' Eur. J.

Pharm. Sci., 22, 315-323, in Guggi, D., Krauland, A. H., and Bernkop-Schnürch, A. (2003) 'Systemic peptide delivery via the stomach: in vivo evaluation of an oral dosage form for salmon calcitonin'. J. Control. Rel. 92, 125-135, and in Bernkop-Schnurch, A., Pinter, Y., Guggi, D., Kahlbacher, H., Schöffmann, G., Schuh, M., Schmerold, I., Del Curto, M. D., D'Antonio, M., Esposito, P. and Huck, Ch. (2005) 'The use of thiolated polymers as carrier matrix in oral peptide delivery'—Proof of concept. J. Control. Release, 106, 26-33.

The active compound may be formulated in seamless micro-spheres as described in WO2004/084870 where the active pharmaceutical ingredient is solubilised as an emulsion, microemulsion or suspension, formulated into minispheres; and variably coated either by conventional or novel coating technologies. The result is an encapsulated drug in "pre-solubilised" form which when administered orally provides for predetermined instant or sustained release of the active drug to specific locations and at specific rates along the gastrointestinal tract. In essence, pre-solubilization of the drug enhances the predictability of its kinetic profile while simultaneously enhancing permeability and drug stability.

One may employ chitosan coated nanocapsules as described in US2009/0074824. The active molecule administered with this technology is protected inside the nanocapsules since they are stable against the action of the gastric fluid. In addition, the mucoadhesive properties of the system enhances the time of adhesion to the intestine walls (it has been verified that there is a delay in the gastrointestinal transit of these systems) facilitating a more effective absorption of the active molecule.

Methods developed by TSRl Inc. may be used. These include Hydrophilic Solubilization Technology (HST) in which gelatin, a naturally derived collagen extract carrying both positive and negative charges, coats the particles of the active ingredient contained in lecithin micelles and prevents their aggregation or clumping. This results in an improved wettability of hydrophobic drug particles through polar interactions. In addition, the amphiphilic lecithin reduces surface tension between the dissolution fluid and the particle surface.

The active ingredient may be formulated with cucurbiturils as excipients.

Alternatively, one may employ the GIPET technology of Merrion Pharmaceuticals to produce enteric coated tablets containing the active ingredient with an absorption enhancer which may be a medium chain fatty acid or a medium chain fatty acid derivative as described in US2007/0238707 or a membrane translocating peptide as described in US7268214.

One may employ GIRES™ technology which consists of a controlled-release dosage form inside an inflatable pouch, which is placed in a drug capsule for oral administration. Upon dissolution of the capsule, a gas-generating system inflates the pouch in the stomach. In clinical trials the pouch has been shown to be retained in the stomach for 16-24 hours.

Alternatively, the active may be conjugated to a protective modifier that allows it to withstand enzymatic degradation in the stomach and facilitate its absorption. The active may be conjugated covalently with a monodisperse, short-chain methoxy polyethylene glycol glycolipids derivative that is crystallized and lyophilized into the dry active pharmaceutical ingredient after purification. Such methods are described in U.S. Pat. No. 5,438,040.

One may also employ a hepatic-directed vesicle (HDV) for active delivery. An HDV may consist of liposomes (≤150 nm diameter) encapsulating the active, which also contain a hepatocyte-targeting molecule in their lipid bilayer. The targeting molecule directs the delivery of the encapsulated active to the liver cells and therefore relatively minute amounts of active are required for effect. Such technology is described in US2009/0087479.

The active may be incorporated into a composition containing additionally a substantially non-aqueous hydrophilic medium comprising an alcohol and a cosolvent, in association with a medium chain partial glyceride, optionally in admixture with a long-chain PEG species as described in US2002/0115592 in relation to insulin.

Alternatively, use may be made of intestinal patches as described in Shen Z, Mitragotri S, Pharm Res. 2002 April; 19(4):391-5 'Intestinal patches for oral drug delivery'.

The active may be incorporated into an erodible matrix formed from a hydrogel blended with a hydrophobic polymer as described in U.S. Pat. No. 7,189,414.

Suitable oral dosage levels for adult humans to be treated may be in the range of 0.05 to 5 mg, preferably about 0.1 to 2.5 mg.

The frequency of dosage treatment of patients may be from 1 to six times daily, for instance from two to four times daily. Treatment will desirably be maintained over a prolonged period of at least 6 weeks, preferably at least 6 months, preferably at least a year, and optionally for life.

Combination treatments for relevant conditions may be carried out using a composition according to the present disclosure and separate administration of one or more other therapeutics. Alternatively, the composition according to the present disclosure may incorporate one or more other therapeutics for combined administration.

Combination therapies according to the present disclsoure include combinations of an active compound as described with insulin, GLP-2, GLP-1, GIP, or amylin, or generally with other anti-diabetics. Thus combination therapies including co-formulations may be made with insulin sensitizers including biguanides such as Metformin, Buformin and Phenformin, TZD's (PPAR) such as Balaglitazone, Pioglitazone, Rivoglitazone, Rosiglitazone and Troglitazone, dual PPAR agonists such as Aleglitazar, Muraglitazar and Tesaglitazar, or secretagogues including sulphonylureas such as Carbutamide, Chloropropamide, Gliclazide, Tolbutamide, Tolazamide, Glipizide, Glibenclamide, Glyburide, Gliquidone, Glyclopyramide and Glimepriride, Meglitinides/glinides (K+) such as Nateglinide, Repaglinide and Mitiglinide, GLP-1 analogs such as Exenatide, Liraglutide and Albiglutide, DPP-4 inhibitors such as Alogliptin, Linagliptin, Saxagliptin, Sitagliptin and Vildagliptin, insulin analogs or special formulations such as (fast acting) Insulin lispro, Insulin aspart, Insulin glulisine, (long acting) Insulin glargine, Insulin detemir), inhalable insulin—Exubra and NPH insulin, and others including alpha-glucosidase inhibitors such as Acarbose, Miglitol and Voglibose, amylin analogues such as Pramlintide, SGLT2 inhibitors such as Dapagliflozin, Remogliflozin and Sergliflozin as well as miscellaneous ones including Benfluorex and Tolrestat.

Further combinations include co-administration or co-formulation with leptins. Leptin resistance is a well-established component of type 2 diabetes; however, injections of leptin have so far failed to improve upon this condition. In contrast, there is evidence supporting that amylin, and thereby molecules with amylin-like abilities, as the salmon calcitonin mimetics, are able to improve leptin sensitivity. Amylin/leptin combination has shown a synergistic effect on body weight and food intake, and also insulin resistance [Kusakabe T et al]. Accordingly, the present disclosure provides a compound of the formula Ac-CSNLSTCVLG KLSQELHKLQ TYPRTDVGAN AP-NH$_2$ (SEQ ID NO:15), which will be referred to herein as 'calcitonin mimetic 1' or 'UGP302'.

Accordingly, the present disclosure includes a pharmaceutical formulation of such a peptide for enteral administration, e.g. for treating type I diabetes, type II diabetes, or metabolic syndrome, or for mitigating insulin resistance, or for reducing an undesirably high fasting serum glucose level, or for reducing an undesirably high peak serum glucose level, or for reducing an undesirably high peak serum insulin level, or for reducing an undesirably high response to a glucose tolerance test, or for treating osteoporosis, or for treating osteoarthritis. The formulation may comprise also a carrier serving to enable effective enteral administration of said active compound.

Preferably, said formulation is formulated for oral administration to the digestive tract.

Preferably, said carrier comprises 5-CNAC, SNAD, or SNAC.

Additionally, the present disclosure includes said peptides as new compounds.

The presently disclosed embodiments is described in the following Examples, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to make and use the described embodiments, and are not intended to limit the scope of the present disclosure nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES

Example 1

Chronic Effect of Calcitonin Mimetic 1 (CM1) Compared to sCT Animals

The study was performed in male Levin-DIO rats (diet-sensitive) and Levin-DR (diet-resistant) (TacLevin: CD (SD) DIO) (Taconic, Hudson, N.Y., U.S.A.) obtained at age 6-7 weeks. On arrival, DIO rats were given high fat diet (60 kcal %) (#D12495, Research Diets Inc., New Brunswick, N.J., USA) and kept on the same diet for 16 weeks prior to and during the experiment. DR rats were given low-fat diet and served as control group. Animals were pair-wise housed throughout the study. Rats were handled and pre-dosed once daily with MilliQ $H_2O$ for 2-3 weeks prior to experimental start to reduce stress-induced hyperglycaemia. Baseline parameters were recorded in an fasting (6 h) condition. Rats were randomized into treatment groups based on fasting body weight (BW) and fasting plasma glucose (FPG). Body weight, food and water intake were recorded once weekly during the study period.

Compound

Oral sCT or calcitonin mimetic 1 solution was prepared on the day of dosing by mixing a carrier with the given compound based on the following calculations:

5-CNAC (vehicle):
Animals treated with oral 5-CNAC received a dose of 150 mg/kg dissolved in milliQ $H_2O$.

Dosage-level for 5-CNAC: 150 mg/kg
Dosing volume: 5 ml/kg
Compound concentration: 30 mg/ml
sCT/Calcitonin Mimetic 1:
Animals treated with oral sCT or oral calcitonin mimetic 1 received doses of 1.0 mg/kg combined with 150 mg/kg 5-CNAC—all dissolved in milliQ $H_2O$.
Dosage-level for sCT/calcitonin mimetic 1: 1.0 mg/kg
Dosing volume: 5 ml/kg
Compound concentration: 0.2 mg/ml Drug administration by per oral (p.o.) gavage b.i.d. (7-8 am and 3-4 pm) during the study period and as single dose in the morning prior to start of OGTT.

Oral gavage of glucose during OGTT was prepared by the following calculation:
D-Glucose:
Animals were given 2 g/kg single dose dissolved in milliQ $H_2O$.
Dosage-level for D-Glucose: 2 g/kg
Dosing volume: 4 ml/kg
Compound concentration: 500 mg/ml
Experimental Setup

| Baseline | Week 1 | Week 2 | Week 3 | Week 4 |
| --- | --- | --- | --- | --- |
| FPG | BW | BW | BW | BW |
| BW | Food | Food | Food | Food |
| B | | FPG | | FPG |
| | | B | | B |
| | | OGTT | | |

FPG Fasting Plasma Glucose
BW Body Weight
B Blood
OGTT Oral Glucose Tolerance Test OGTT Following Overnight Fasting (16 h):

| −30 | 0 | 15 | 30 | 60 | 120 | 240 min |
| --- | --- | --- | --- | --- | --- | --- |
| D | G | B | B | B | B | B |
| B | B | BG | BG | BG | BG | BG |
| BG | BG | | | | | |

D = Drug;
BG = Blood glucose;
B = Blood;
G = Glucose

Blood sampling and glycemia were measured by heated tail venous puncture.

Whole blood glucose levels were determined with an ACCU-CHEK® Avia blood glucose meter (Roche Diagnostics, Rotkreuz, Switzerland). Blood (approx 300 ul) is collected in 1 ml MiniCollect K3EDTA plasma-tube (Greiner-Bio-One GmbH, Frickenhausen, Germany), inverted, and stored on ice. Tubes are centrifuged 3000×g (5000 rpm in table centrifuge) for 10 min at 4° C. and plasma obtained. Plasma samples are stored at −20° C. until analysis. A total of ~2.5 ml blood is obtained during OGTT (~0.3% of body weight).

Experimental Groups

| Intervention | Compound | Conc. | Number |
| --- | --- | --- | --- |
| Oral vehicle | 5-CNAC | 150 mg/kg | n = 10 |
| Oral sCT | 5-CNAC + sCT | 150 mg/kg + 1 mg/kg | n = 10 |

-continued

| Intervention | Compound | Conc. | Number |
| --- | --- | --- | --- |
| Oral calcitonin mimetic 1 | 5-CNAC + calcitonin mimetic 1 | 150 mg/kg 1 mg/kg | n = 10 |

Statistics

Statistical analysis was performed by one-way ANOVA followed by the Dunnett's post hoc test for multiple comparison. Student's t-test was performed to compare two paired group. All analysis was performed using GRAPHPAD PRISM software (GraphPad Prism, San Diego, Calif. U.S.A). Incremental area under curve (iAUC) during OGTT was calculated by the trapezoidal method. A value of P<0.05 was considered to be significant. All data are presented as mean±standard error of the mean (SEM).

3. Results

Baseline Characteristics

Figure 2A:
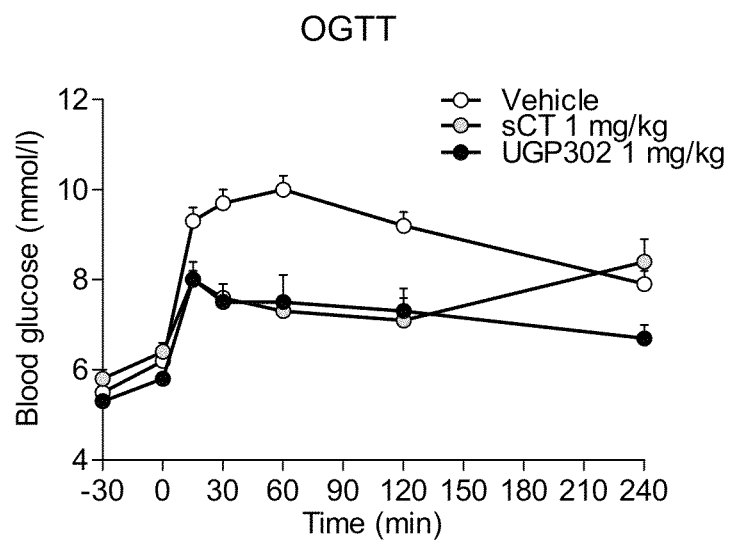
FIGS. 2A and 2B show the effect of oral sCT versus oral UGP 302 on glucose tolerance during OGTT in DIO rats as measured in Example 1.
Figure 2B:
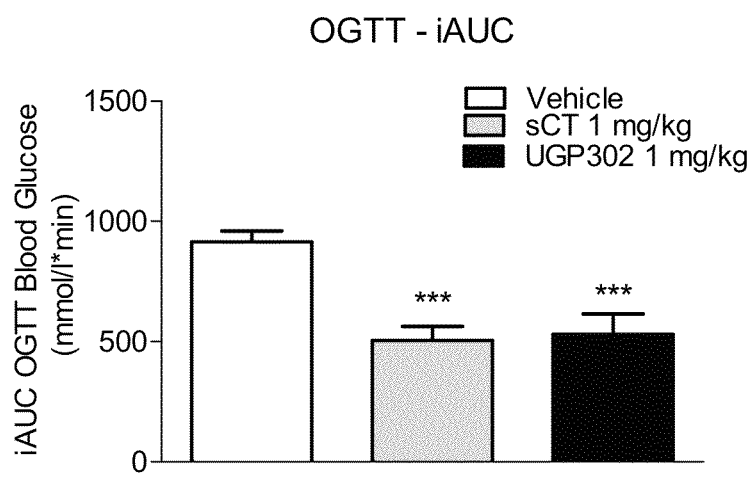
Figure 3:
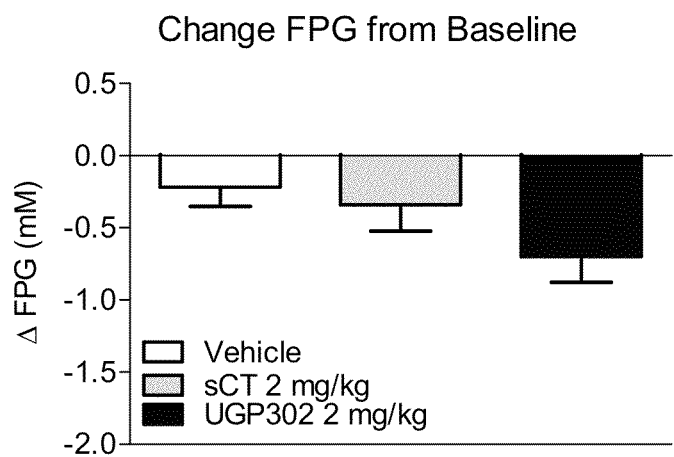
FIG. 3 shows the effect of oral sCT versus oral UGP 302 on fasting glycemia in DIO rats as measured in Example 1.

Results are summarized in FIG. 1 (Food intake and body weight), FIG. 2 (OGTT) and FIG. 3 (FPG). FIGS. 1A-D show the effect of chronic oral salmon calcitonin ("sCT") versus oral UGP 302 administration on body weight and food intake in DIO rats as measured in Example 1. FIGS. 2A and 2B show the effect of oral sCT versus oral UGP 302 on glucose tolerance during OGTT in DIO rats as measured in Example 1. FIG. 3 shows the effect of oral sCT versus oral UGP 302 on fasting glycemia in DIO rats as measured in Example 1;

One dose of oral sCT/calcitonin mimetic 1 containing 1 mg/kg compound was applied by gavage twice daily to four groups of rats for 4 weeks. An oral vehicle group served as dosing regimen control, respectively. * P<0.05,  P<0.01, * P<0.001 vs Vehicle. Results are presented as means±SEM.

The 16-weeks ad libitum high-fat diet induced a pronounced obese phenotype in the diet-sensitive (DIO) rats when comparing body weight to their diet-resistant (DR) littermates (P<0.001) (Table 1). 6-hrs Fasting glycemia was not different between DIO and DR. In contrast, area under curve (AUC) calculations during OGTT was significantly higher in DIO rats compared to DR rats, demonstrating the high-fat diet-induced glucose intolerance (Table 1).

TABLE 1

Metabolic parameters in DIO and DR rats

| | Diet-resistant (DR) | Diet-sensitive (DIO) |
| --- | --- | --- |
| Body Weight (g) | 609.5 ± 24.5 | 841.8 ± 22.9*** |
| Fasting plasma glucose (mM) | 6.5 ± 0.1 | 6.8 ± 0.2 |
| AUC in OGTT Blood glucose (mM * min) | 625.1 ± 20.5 | 914.3 ± 44.6*** |

AUC, area under curve;
OGTT, oral glucose tolerance test.
Data are means ± SEM (n = 12/DR, n = 24/DIO).

Body Weight and Food Intake

During the first week of treatment administration of oral sCT significantly reduced food intake compared to oral vehicle treated rats. Furthermore, oral sCT protected against further gain in body weight as observed for oral vehicle group (FIG. 1). Thus, these observations confirm the acute strong anorectic action induced by application of oral sCT in DIO rats. Interestingly, from week 2 of treatment and throughout the study period, food intake normalized in oral sCT treated rats and resembled ingestion by oral vehicle resulting in a lack of difference in regards to cumulative food intake at study end. This confirms previously reports suggesting a transient effect of oral sCT upon energy intake. However, throughout the study period, oral sCT sustained the protecting effect on body weight gain and significantly reduced body weight from baseline when compared to oral vehicle at study end (FIG. 1). This is in line with a possibly endogenous effect of oral sCT upon energy expenditure to chronically regulate energy balance.

Generally, oral application of calcitonin mimetic 1 resembled the strong anorectic action of oral sCT during the initial week of treatment and significantly reduced food intake and protected against gain in body weight compared to oral vehicle group (FIG. 1).

As observed for oral sCT, calcitonin mimetic 1 exerted a transient effect on food intake, although food intake trended reduced when compared to oral sCT during the study period. Thus, following four weeks of treatment cumulative food intake was significantly reduced in calcitonin mimetic 1 when compared to oral vehicle. Furthermore, when compared to oral sCT, a more pronounced significant reduction in body weight was observed suggesting superiority in regards to effect on energy balance.

Glucose Tolerance

Results are shown in FIG. 2. One dose of oral sCT/calcitonin mimetic 1 containing 1 mg/kg compound were applied by gavage twice daily to four groups of rats for 4 weeks. An oral vehicle group served as dosing regimen control. OGTT performed following 2 weeks of treatment after overnight-fasting. *** P<0.001 vs Vehicle. Results are presented as means±SEM.

Oral sCT significantly reduced glucose iAUC during OGTT after 2 weeks of treatment compared to oral vehicle (FIG. 2), thus confirming the postprandial glycemic control exerted by oral application of sCT as previously demonstrated. In general, calcitonin mimetic 1 demonstrated a similar significant reduction in iAUC as observed for oral sCT, although with no clear superiority to oral sCT in this respect.

Fasting Glycaemia

Following 2 and 4 weeks of treatment, oral sCT application was not significantly different from oral vehicle treated rats, which is in contrast with previously observations in male DIO rats, in where a 1-1.5 mM reduction in fasting blood glucose typically is observed following chronic treatment. For calcitonin mimetic 1, a trend towards superiority in fasting glycaemia was observed throughout the study period when compared to oral vehicle or oral sCT.

Example 2

Acute and Short Term Effects of Oral sCT Versus Oral Calcitonin Mimetic 1

Animals

The study was performed in male Levin-DIO rats (diet-sensitive) and Levin-DR (diet-resistant) (TacLevin: CD (SD) DIO) (Taconic, Hudson, N.Y., U.S.A.) obtained at age 6-7 weeks. On arrival, DIO rats were given high fat diet (60 kcal %) (#D12495, Research Diets Inc., New Brunswick, N.J., USA) and kept on the same diet for 12 weeks prior to and during the experiment. DR rats were given low-fat diet and served as control group. Animals were pair-wise housed throughout the study. Rats were handled and pre-dosed once daily with MilliQ H2O for 2-3 weeks prior to experimental start to reduce stress-induced hyperglycaemia. On the day prior to study start animals were given a single dose of vehicle. Baseline parameters were recorded in an overnight fasting (16 h) condition. Rats were randomized into treatment groups based on fasting body weight (BW) and fasting plasma glucose (FPG). Body weight, food and water intake were recorded prior to and at study end.

Compounds

Oral sCT/calcitonin mimetic 1 solution was prepared on the day of dosing by mixing the carrier with the given compound based on the following calculations:

5-CNAC (vehicle):

Animals treated with oral 5-CNAC received a dose of 150 mg/kg dissolved in milliQ H20.
Dosage-level for 5-CNAC: 150 mg/kg
Dosing volume: 5 ml/kg
Compound concentration: 30 mg/ml sCT/calcitonin mimetic 1:

Animals treated with oral sCT or oral calcitonin mimetic 1 received doses of 0.5 mg/kg, 1.0 mg/kg or 2.0 mg/kg combined with 150 mg/kg 5-CNAC—all dissolved in milliQ H20.
Dosage-level for sCT/calcitonin mimetic 1:
 0.5 mg/kg
Dosing volume: 5 ml/kg
Compound concentration: 0.1 mg/ml
Dosage-level for sCT/calcitonin mimetic 1:
 1.0 mg/kg
Dosing volume: 5 ml/kg
Compound concentration: 0.2 mg/ml
Dosage-level for sCT/calcitonin mimetic 1:
 2.0 mg/kg
Dosing volume: 5 ml/kg
Compound concentration: 0.4 mg/ml Drug administration were given by per oral (p.o.) gavage b.i.d. during the study period and as single dose in the morning prior to start of OGTT.

Oral gavage of glucose during OGTT was prepared by the following calculation:

D-Glucose:

Animals were given 2 g/kg single dose dissolved in milliQ H20.
Dosage-level for D-Glucose: 2 g/kg
Dosing volume: 4 ml/kg
Compound concentration: 500 mg/ml Experimental Setup Acute Testing—Treatment Period for 0.5 mg/kg, 1 mg/kg and 2 mg/kg:

| Day 0 | Day 1-2 | Day 3 | Day 4 | Day 5 | Day 6 | Day 7 |
|---|---|---|---|---|---|---|
| $1^{st}$ OGTT All vehicle | Rest No handling | Pre-dose All vehicle | Treatment (b.i.d) | Treatment (b.i.d) | Treatment (b.i.d) | $2^{nd}$ OGTT Single dose |

Following the initial ($1^{st}$) OGTT, animals are randomized into treatment groups based on FBG and BW. Animals will be pre-treated 3 days (b.i.d.) prior to $2^{nd}$ OGTT. Dosing will be performed in the morning (7-8 am) and afternoon (3-4 pm).

The study was performed in an x-over design with each animal being its own control.

OGTT Following Overnight Fasting (16 h):

| −30 | 0 | 15 | 30 | 60 | 120 | 240 min |
|---|---|---|---|---|---|---|
| D B BG | G B BG | B BG | B BG | B BG | B BG | B BG |

D = Drug;
BG = Blood glucose;
B = Blood;
G = Glucose

Blood sampling and glycemia were measured by heated tail venous puncture.

Whole blood glucose levels were determined with an ACCU-CHEK® Avia blood glucose meter (Roche Diagnostics, Rotkreuz, Switzerland). Blood (approx 300 ul) is collected in 1 ml MiniCollect K3EDTA plasma-tube (Greiner-Bio-One GmbH, Frickenhausen, Germany), inverted, and stored on ice. Tubes are centrifuged 3000×g (5000 rpm in table centrifuge) for 10 min at 4° C. and plasma obtained. Plasma samples are stored at −20° C. until analysis. A total of ~2.5 ml blood is obtained during OGTT (~0.3% of body weight).

Experimental Groups

| Intervention | Compound | Conc. | Number |
|---|---|---|---|
| Oral vehicle | 5-CNAC | 150 mg/kg | (4 groups of n = 8) X-over design to 0.5 mg/kg |
| Oral sCT | 5-CNAC + sCT | 150 mg/kg + 0.5 mg/kg | n = 8 |
| Oral calcitonin mimetic 1 | 5-CNAC + calcitonin mimetic 1 | 150 mg/kg 0.5 mg/kg | n = 8 |
| Oral vehicle | 5-CNAC | 150 mg/kg | (4 groups of n = 8) X-over design to 1 mg/kg |
| Oral sCT | 5-CNAC + sCT | 150 mg/kg + 1 mg/kg | n = 8 |
| Oral calcitonin mimetic 1 | 5-CNAC + calcitonin mimetic 1 | 150 mg/kg 1 mg/kg | n = 8 |
| Oral vehicle | 5-CNAC | 150 mg/kg | (4 groups of n = 8) X-over design to 2 mg/kg |
| Oral sCT | 5-CNAC + sCT | 150 mg/kg + 2 mg/kg | n = 8 |
| Oral calcitonin mimetic 1 | 5-CNAC + calcitonin mimetic 1 | 150 mg/kg 2 mg/kg | n = 8 |

Statistics

Statistical analysis was performed by one-way ANOVA followed by the Dunnett's post hoc test for multiple comparison. Student's t-test was performed to compare two paired group. All analysis was performed using GRAPHPAD PRISM software (GraphPad Prism, San Diego, Calif. U.S.A). Incremental area under curve (iAUC) during OGTT was calculated by the trapezoidal method. A value of $P<0.05$ was considered to be significant. All data are presented as mean±standard error of the mean (SEM).

3. Results

Baseline Characteristics

The 12-weeks ad libitum high-fat diet induced a pronounced obese phenotype in the diet-sensitive (DIO) rats when comparing body weight to their diet-resistant (DR) littermates ($P<0.001$) (Table 1). Fasting glycemia was not different between DIO and DR. In contrast, area under curve (AUC) calculations during OGTT was significantly higher in DIO rats compared to DR rats, demonstrating the high-fat diet-induced glucose intolerance (Table 2).

TABLE 2

Metabolic parameters in DIO and DR rats

|  | Diet-resistant (DR) | Diet-sensitive (DIO) |
|---|---|---|
| Body Weight (g) | 609.5 ± 24.5 | 813.6 ± 9.8*** |
| Fasting plasma glucose (mM) | 5.8 ± 0.1 | 5.8 ± 0.2 |

TABLE 2-continued

Metabolic parameters in DIO and DR rats

|  | Diet-resistant (DR) | Diet-sensitive (DIO) |
|---|---|---|
| AUC in OGTT Blood glucose (mM * min) | 648.8 ± 27.3 | 888.4 ± 64.3*** |

AUC, area under curve;
OGTT, oral glucose tolerance test.
Data are means ± SEM (n = 12/DR, n = 24/DIO).

Body Weight and Food Intake

Three different doses of oral sCT/calcitonin mimetic 1 containing 0.5, 1 and 2 mg/kg compound were applied by gavage twice daily to 4 groups of rats for 3 days. * P<0.05, ** P<0.01 vs oral sCT.

Figure 4A:
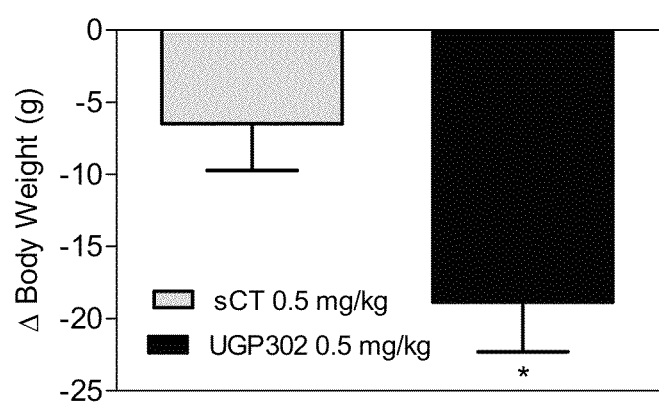
FIGS. 4A and 4B show the effect of oral sCT versus oral UGP 302 on body weight and food intake in DIO rats observed in Example 2 at a first dosage.
Figure 4B:
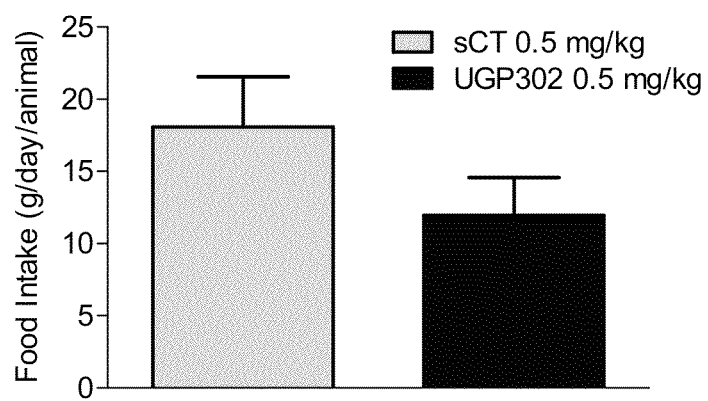
Figure 5A:
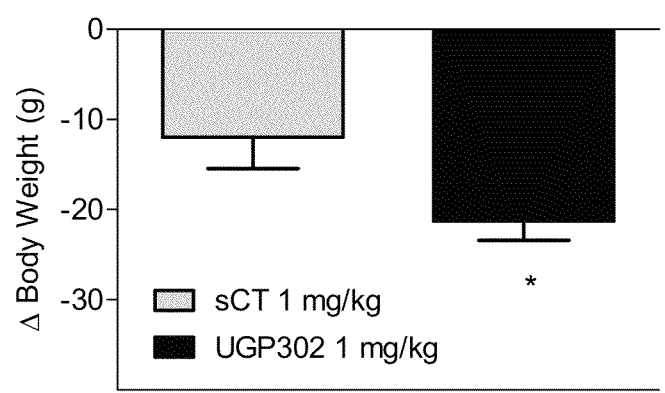
FIGS. 5A and 5B show the effect of oral sCT versus oral UGP 302 on body weight and food intake in DIO rats observed in Example 2 at a second dosage.
Figure 5B:
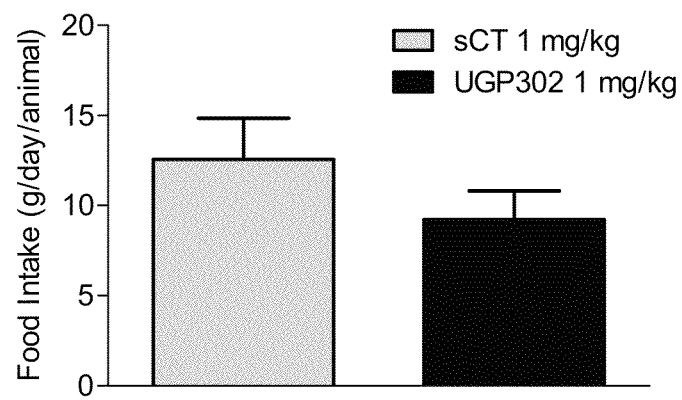
Figure 6A:
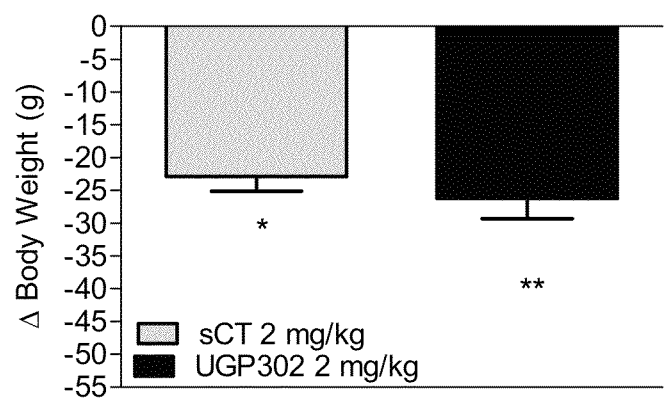
FIGS. 6A and 6B show the effect of oral sCT versus oral UGP 302 on body weight and food intake in DIO rats observed in Example 2 at a third dosage.
Figure 6B:
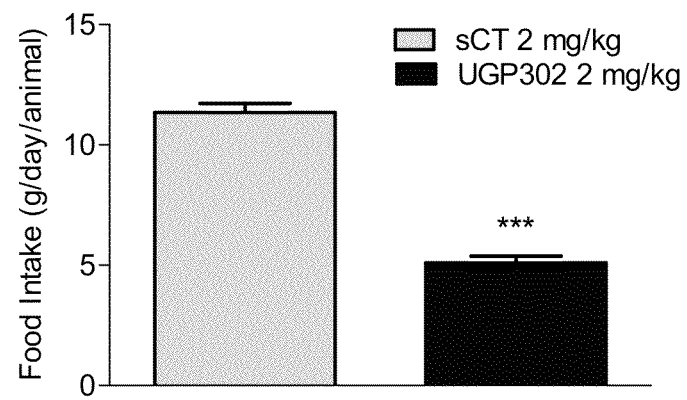

Results are presented in FIGS. 4-6 as means±SEM. FIGS. 4A and 4B show the effect of oral sCT versus oral UGP 302 on body weight and food intake in DIO rats observed in Example 2 at a first dosage. FIGS. 5A and 5B show the effect of oral sCT versus oral UGP 302 on body weight and food intake in DIO rats observed in Example 2 at a second dosage. FIGS. 6A and 6B show the effect of oral sCT versus oral UGP 302 on body weight and food intake in DIO rats observed in Example 2 at a third dosage;

Oral sCT dose-dependently decreased body weight and food intake following the short-term treatment period and thus confirmed the anorectic action induced by targeting the amylin receptor as previously observed. In general, the mimetic demonstrated dose-dependent superiority to oral sCT in regards to reduction in body weight as illustrated in FIGS. 4, 5 and 6. Application of calcitonin mimetic 1 at 0.5 mg/kg demonstrated significantly difference to oral sCT 0.5 mg/kg. The food intake for the mimetic trended dose-dependently reduced compared to oral sCT.

Glucose Tolerance

Figure 7A:
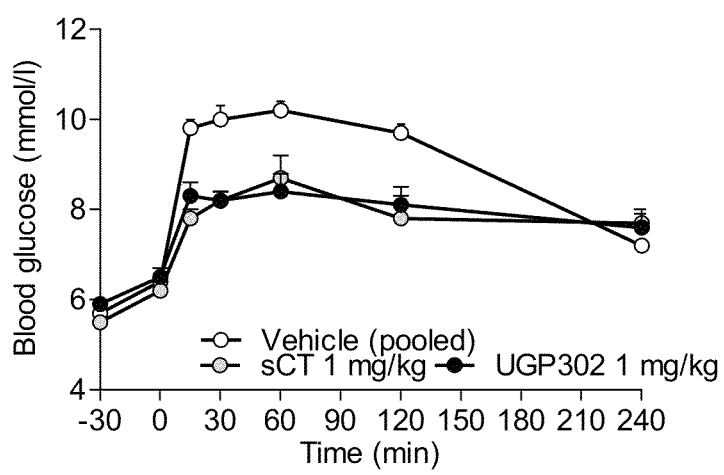
FIGS. 7A and 7B show the effect of oral sCT versus oral UGP 302 at a first dosage on glucose tolerance during OGTT in DIO rats as measured in Example 2.
Figure 7B:
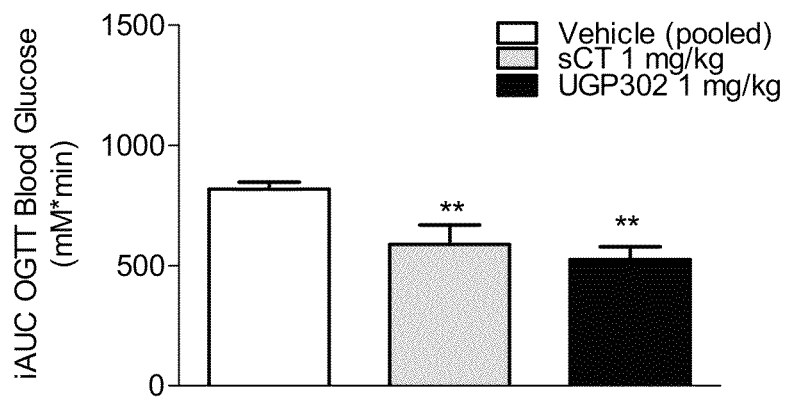
Figure 8A:
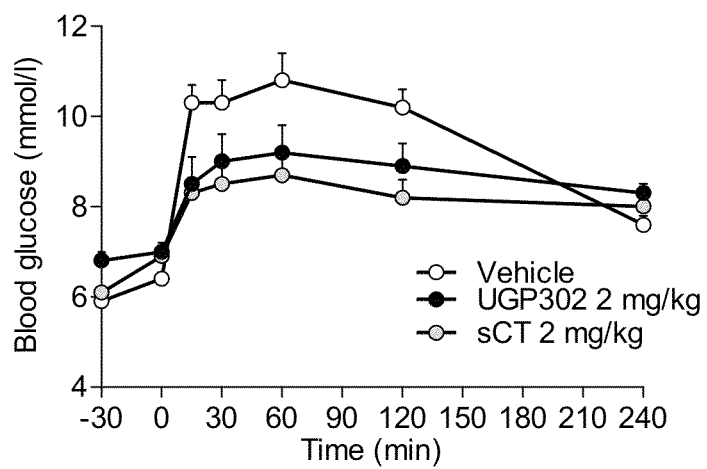
FIGS. 8A and 8B show the effect of oral sCT versus oral UGP 302 at a second dosage on glucose tolerance during OGTT in DIO rats as measured in Example 2.
Figure 8B:
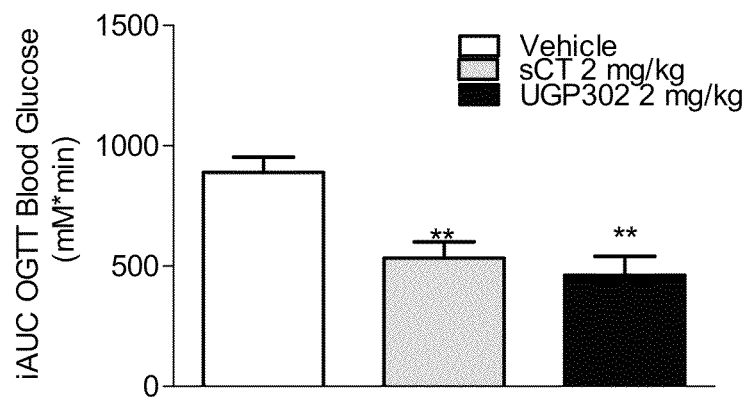
Figure 9A:
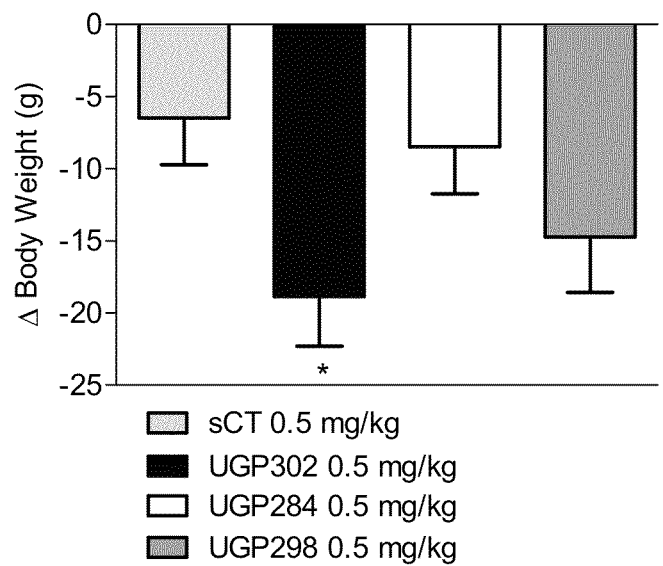
FIGS. 9A-F show the effect of oral sCT versus three oral UGPs on body weight and food intake in DIO rats as measured in Example 3.
Figure 9B:
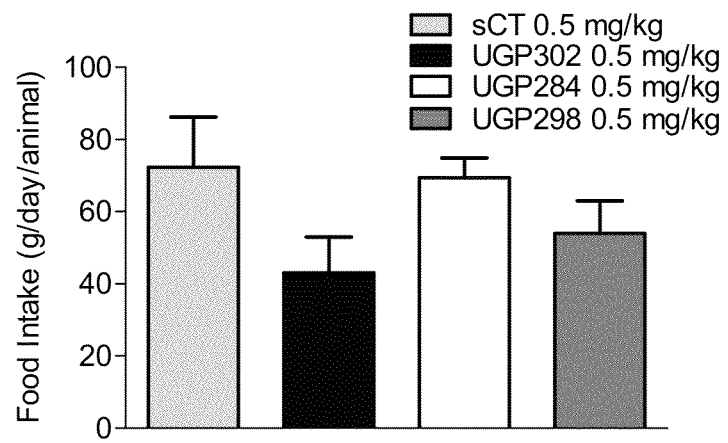
Figure 9C:
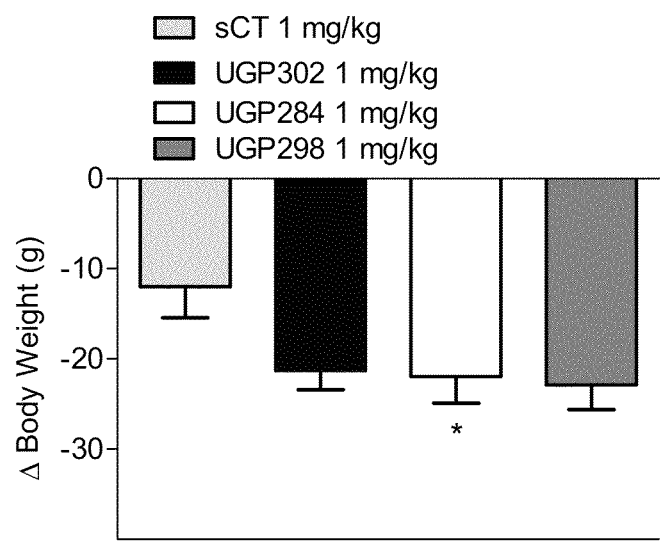
Figure 9D:
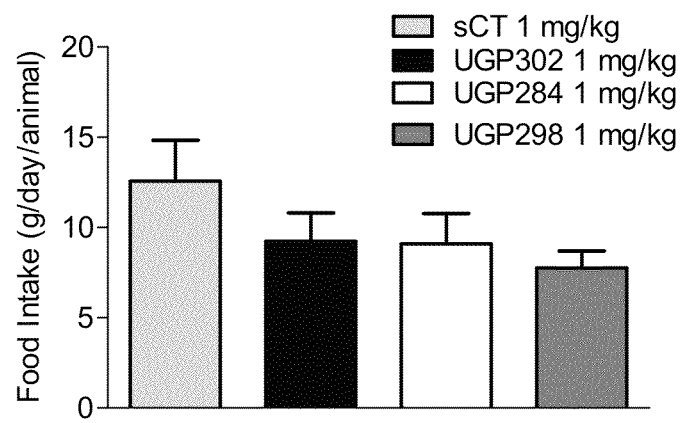
Figure 9E:
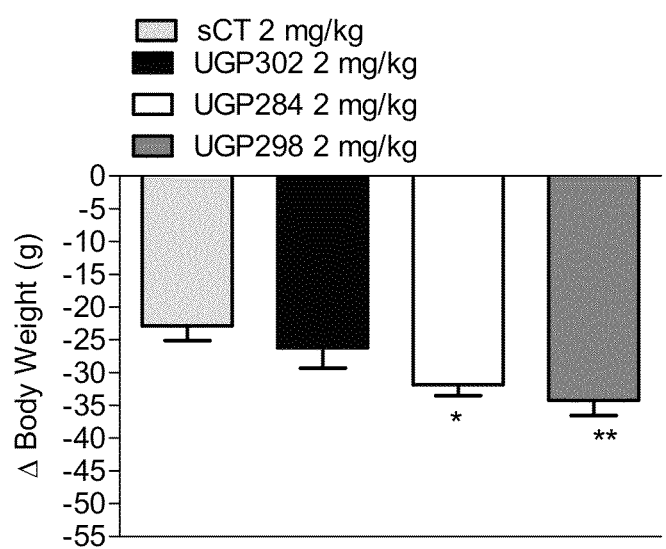
Figure 9F:
Figure 10A:
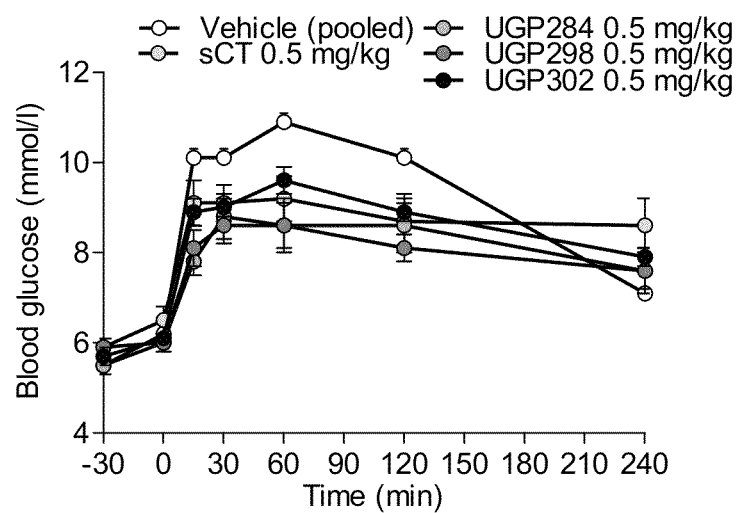
FIGS. 10A-F show the effect of oral sCT versus three oral UGPs on glucose levels in a glucose tolerance test in DIO rats as measured in Example 3.
Figure 10B:
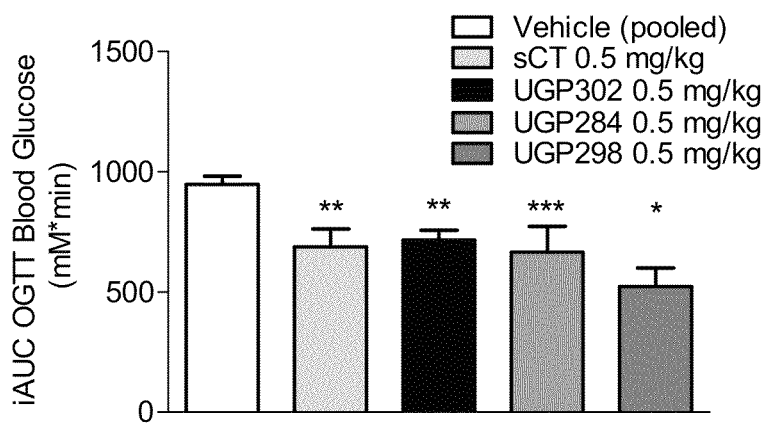
Figure 10C:
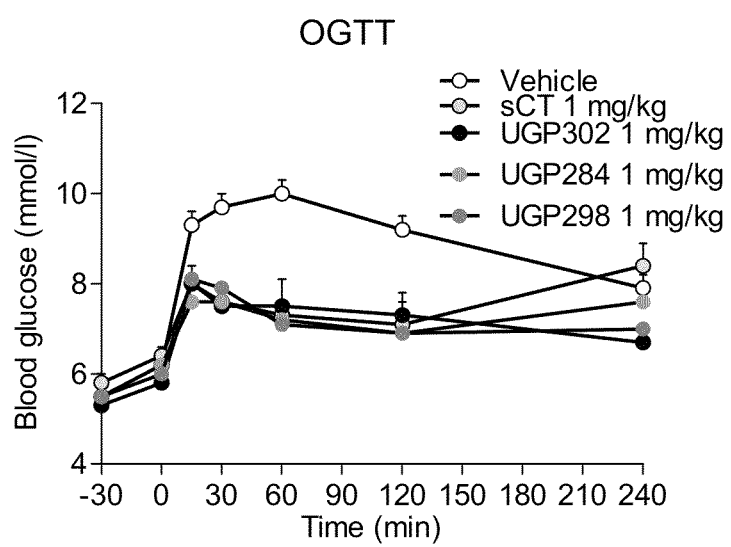
Figure 10D:
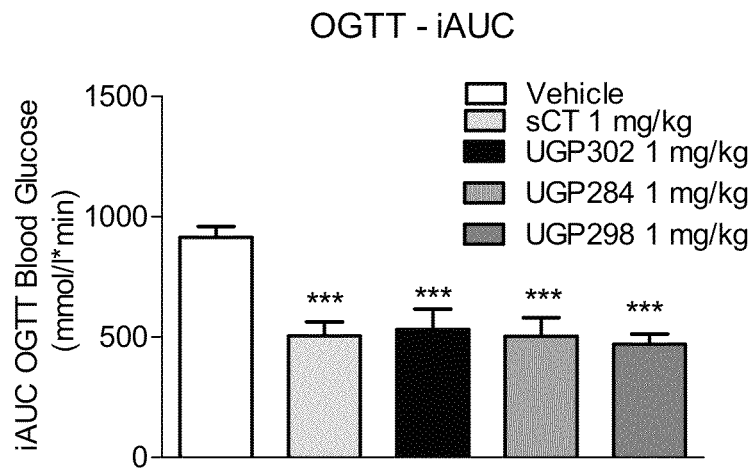
Figure 10E:
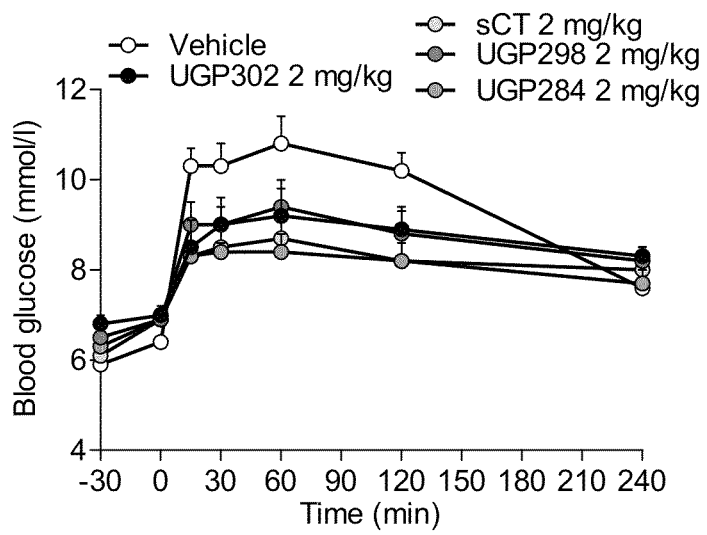
Figure 10F:
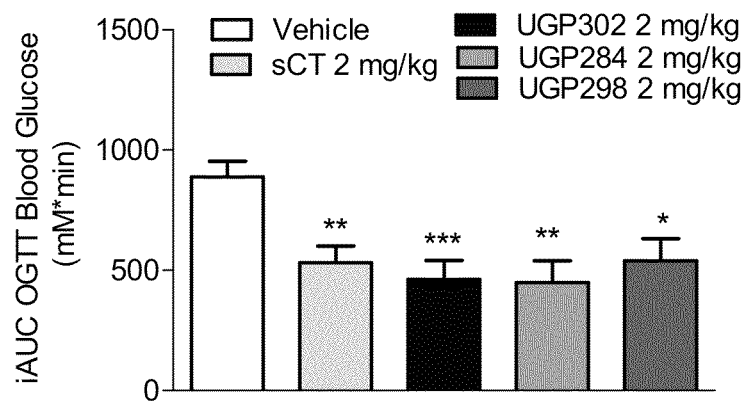

Three different doses of oral sCT/calcitonin mimetic 1 containing 0.5, 1 and 2 mg/kg compound were applied by gavage twice daily to 4 groups of rats for 3 days prior to OGTT. The experimental set-up was a cross-over design. * P<0.05,  P<0.01, * P<0.001 vs oral vehicle. Results are presented in FIGS. 7 and 8 as means±SEM. FIGS. 7A and 7B show the effect of oral sCT versus oral UGP 302 at a first dosage on glucose tolerance during OGTT in DIO rats as measured in Example 2. FIGS. 8A and 8B show the effect of oral sCT versus oral UGP 302 at a second dosage on glucose tolerance during OGTT in DIO rats as measured in Example 2.

Oral sCT significantly reduced glucose iAUC during OGTT for 0.5, 1 and 2 mg/kg doses compared to oral vehicle, thus confirming the postprandial glycemic control exerted by oral application of sCT as previously demonstrated. Calcitonin mimetic 1 demonstrated a similar significantly reduction in iAUC as observed for oral sCT, although with no clear superiority to oral sCT within the various UGPs.

Example 3

Acute and Short Term Effects of Oral sCT Versus UGP284, UGP298 and UGP302

Animals

The study was performed in male Levin-DIO rats (diet-sensitive) and Levin-DR (diet-resistant) (TacLevin: CD (SD) DIO) (Taconic, Hudson, N.Y., U.S.A.) obtained at age 6-7 weeks. On arrival, DIO rats were given high fat diet (60 kcal %) (#D12495, Research Diets Inc., New Brunswick, N.J., USA) and kept on the same diet for 12 weeks prior to and during the experiment. DR rats were given low-fat diet and served as control group. Animals were pair-wise housed throughout the study. Rats were handled and pre-dosed once daily with MilliQ H2O for 2-3 weeks prior to experimental start to reduce stress-induced hyperglycemia. On the day prior to study start animals were given a single dose of vehicle. Baseline parameters were recorded in an overnight fasting (16 h) condition. Rats were randomized into treatment groups based on fasting body weight (BW) and fasting plasma glucose (FPG). Body weight, food and water intake were recorded prior to and at study end.

Compound

Oral sCT/UGP solution was prepared on the day of dosing by mixing the carrier with the given compound based on the following calculations:

5-CNAC (vehicle):

Animals treated with oral 5-CNAC received a dose of 150 mg/kg dissolved in milliQ H20.

Dosage-level for 5-CNAC: 150 mg/kg
Dosing volume: 5 ml/kg
Compound concentration: 30 mg/ml
(sCT/UGP284/UGP298/UGP302)

Animals treated with oral sCT or oral UGP284/UGP298/UGP302 received doses of 0.5 mg/kg, 1.0 mg/kg or 2.0 mg/kg combined with 150 mg/kg 5-CNAC—all dissolved in milliQ $H_2O$.

Dosage-level for sCT/UGP284/UGP298/UGP302: 0.5 mg/kg
Dosing volume: 5 ml/kg
Compound concentration: 0.1 mg/ml
Dosage-level for sCT/UGP284/UGP298/UGP302: 1.0 mg/kg
Dosing volume: 5 ml/kg
Compound concentration: 0.2 mg/ml
Dosage-level for sCT/UGP284/UGP298/UGP302: 2.0 mg/kg
Dosing volume: 5 ml/kg
Compound concentration: 0.4 mg/ml Drug administration were given by per oral (p.o.) gavage b.i.d. during the study period and as single dose in the morning prior to start of OGTT.

Oral gavage of glucose during OGTT was prepared by the following calculation:

D-Glucose:

Animals were given 2 g/kg single dose dissolved in milliQ H20.

Dosage-level for D-Glucose: 2 g/kg
Dosing volume: 4 ml/kg
Compound concentration: 500 mg/ml Experimental Setup Acute Testing—Treatment Period for 0.5 mg/kg, 1 mg/kg and 2 mg/kg:

| Day 0 | Day 1-2 | Day 3 | Day 4 | Day 5 | Day 6 | Day 7 |
|---|---|---|---|---|---|---|
| $1^{st}$ OGTT All vehicle | Rest No handling | Pre-dose All vehicle | Treatment (b.i.d) | Treatment (b.i.d) | Treatment (b.i.d) | $2^{nd}$ OGTT Single dose |

Following the initial ($1^{st}$) OGTT, animals were randomized into treatment groups based on FBG and BW. Animals were pre-treated 3 days (b.i.d.) prior to $2^{nd}$ OGTT. The study was performed in an x-over design with each animal being its own control.

OGTT Following Overnight Fasting (16 h):

| −30 | 0 | 15 | 30 | 60 | 120 | 240 min |
|---|---|---|---|---|---|---|
| D B BG | G B BG | B BG | B BG | B BG | B BG | B BG |

D = Drug;
BG = Blood glucose;
B = Blood;
G = Glucose

Blood sampling and glycemia were measured by heated tail venous puncture. Whole blood glucose levels were determined with an ACCU-CHEK® Avia blood glucose meter (Roche Diagnostics, Rotkreuz, Switzerland). Blood (approx 300 μl) is collected in 1 ml MiniCollect K3EDTA plasma-tube (Greiner-Bio-One GmbH, Frickenhausen, Germany), inverted, and stored on ice. Tubes are centrifuged 3000×g (5000 rpm in table centrifuge) for 10 min at 4° C. and plasma obtained. Plasma samples are stored at −20° C. until analysis. A total of 2.5 ml blood is obtained during OGTT (~0.3% of body weight).

Experimental Groups

| Intervention | Compound | Conc. | Number |
|---|---|---|---|
| Oral vehicle | 5-CNAC | 150 mg/kg | (4 groups of n = 8) X-over design to 0.5 mg/kg |
| Oral sCT | 5-CNAC + sCT | 150 mg/kg + 0.5 mg/kg | n = 8 |
| Oral UGP284 | 5-CNAC + UGP284 | 150 mg/kg + 0.5 mg/kg | n = 8 |
| Oral UGP298 | 5-CNAC + UGP298 | 150 mg/kg + 0.5 mg/kg | n = 8 |
| Oral UGP302 | 5-CNAC + UGP302 | 150 mg/kg + 0.5 mg/kg | n = 8 |
| Oral vehicle | 5-CNAC | 150 mg/kg | (4 groups of n = 8) X-over design to 1 mg/kg |
| Oral sCT | 5-CNAC + sCT | 150 mg/kg + 1 mg/kg | n = 8 |
| Oral UGP284 | 5-CNAC + UGP284 | 150 mg/kg + 1 mg/kg | n = 8 |
| Oral UGP298 | 5-CNAC + UGP298 | 150 mg/kg + 1 mg/kg | n = 8 |
| Oral UGP302 | 5-CNAC + UGP302 | 150 mg/kg + 1 mg/kg | n = 8 |
| Oral vehicle | 5-CNAC | 150 mg/kg | (4 groups of n = 8) X-over design to 2 mg/kg |
| Oral sCT | 5-CNAC + sCT | 150 mg/kg + 2 mg/kg | n = 8 |
| Oral UGP284 | 5-CNAC + UGP284 | 150 mg/kg + 2 mg/kg | n = 8 |
| Oral UGP298 | 5-CNAC + UGP298 | 150 mg/kg + 2 mg/kg | n = 8 |
| Oral UGP302 | 5-CNAC + UGP302 | 150 mg/kg + 2 mg/kg | n = 8 |

Statistics

Statistical analysis was performed by one-way ANOVA followed by the Dunnett's post hoc test for multiple comparison. Student's t-test was performed to compare two paired group. All analysis was performed using GRAPHPAD PRISM software (GraphPad Prism, San Diego, Calif. U.S.A). Incremental area under curve (iAUC) during OGTT was calculated by the trapezoidal method. A value of $P<0.05$ was considered to be significant. All data are presented as mean±standard error of the mean (SEM).

3. Results
Baseline Characteristics

The 12-weeks ad libitum high-fat diet induced a pronounced obese phenotype in the diet-sensitive (DIO) rats when comparing body weight to their diet-resistant (DR) littermates ($P<0.001$) (Table 3). Fasting glycemia was not different between DIO and DR. In contrast, area under curve (AUC) calculations during OGTT were significantly higher in DIO rats compared to DR rats, demonstrating the high-fat diet-induced glucose intolerance (Table 3).

TABLE 3

Metabolic parameters in DIO and DR rats

| | Diet-resistant (DR) | Diet-sensitive (DIO) |
|---|---|---|
| Body Weight (g) | 609.5 ± 24.5 | 813.6 ± 9.8*** |
| Fasting plasma glucose (mM) | 5.8 ± 0.1 | 5.8 ± 0.2 |
| AUC in OGTT Blood glucose (mM * min) | 648.8 ± 27.3 | 888.4 ± 64.3*** |

AUC, area under curve;
OGTT, oral glucose tolerance test.
Data are means ± SEM (n = 12/DR, n = 24/DIO).

Body Weight and Food Intake

Oral sCT dose-dependently decreased body weight and food intake following the short-term treatment period and thus confirmed the anorectic action induced by targeting the amylin receptor as previously observed. In general, all UGP mimetics demonstrated dose-dependently superiority to oral sCT in regards to reduction in body weight as illustrated in FIG. 9. Application of UGP302 at 0.5 mg/kg demonstrated significantly difference to oral sCT 0.5 mg/kg. For UGP284, significantly difference at 2 mg/kg dose was observed when compared to oral sCT 2 mg/kg. Finally, UGP298 at both 1 mg/kg and 2 mg/kg doses were significantly different when compared with oral sCT at similar doses (FIG. 9). FIGS. 9A-9F show the effect of three different doses of oral sCT/UGP284/UGP298/UGP302 containing 0.5, 1 and 2 mg/kg compound were applied by gavage twice daily to 4 groups of rats for 3 days. * $P<0.05$, ** $P<0.01$ vs oral sCT. Results are presented as means±SEM.

Glucose Tolerance

FIGS. 10A-10F show the effect of oral sCT versus oral UGPs on glucose tolerance during OGTT in DIO rats. Three different doses of oral sCT/UGP284/UGP298/UGP302 containing 0.5, 1 and 2 mg/kg compound were applied by gavage twice daily to 4 groups of rats for 3 days prior to OGTT. The experimental set-up was a cross-over design. * $P<0.05$,  $P<0.01$, * $P<0.001$ vs oral vehicle. Results are presented as means±SEM.

All UGPs demonstrated a similar significant reduction in iAUC as observed for oral sCT (FIG. 10).

In conclusion, application of UGP284, UGP298 and UGP302 at 0.5, 1 and 2 mg/kg doses demonstrated superiority to equivalent doses of oral sCT in regards to energy balance in male DIO rats. Furthermore, UGP284, UGP298 and UGP302 at doses of 0.5, 1 and 2 mg/kg produced an improvement in glucose tolerance during OGTT.

Example 4

Figure 11:
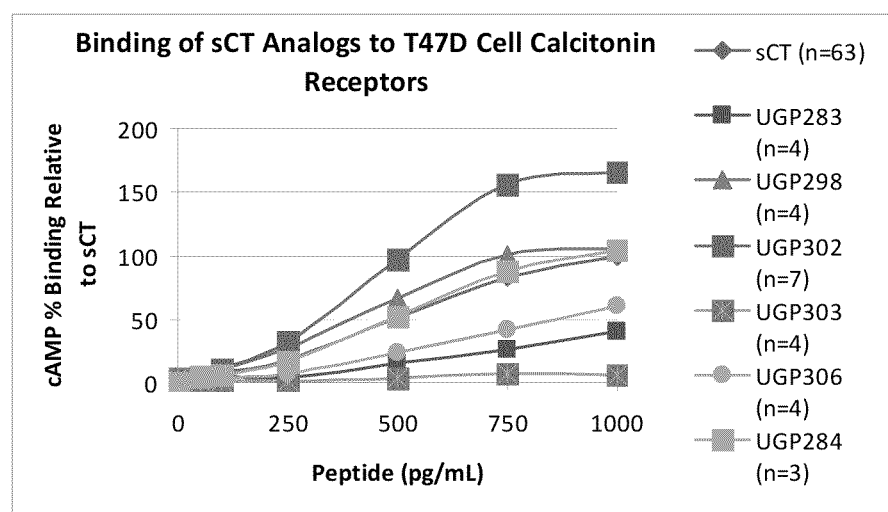
FIG. 11 shows binding results for six UGP compounds to T47D cell calcitonin receptors as measured in Example 4.
Figure 12:
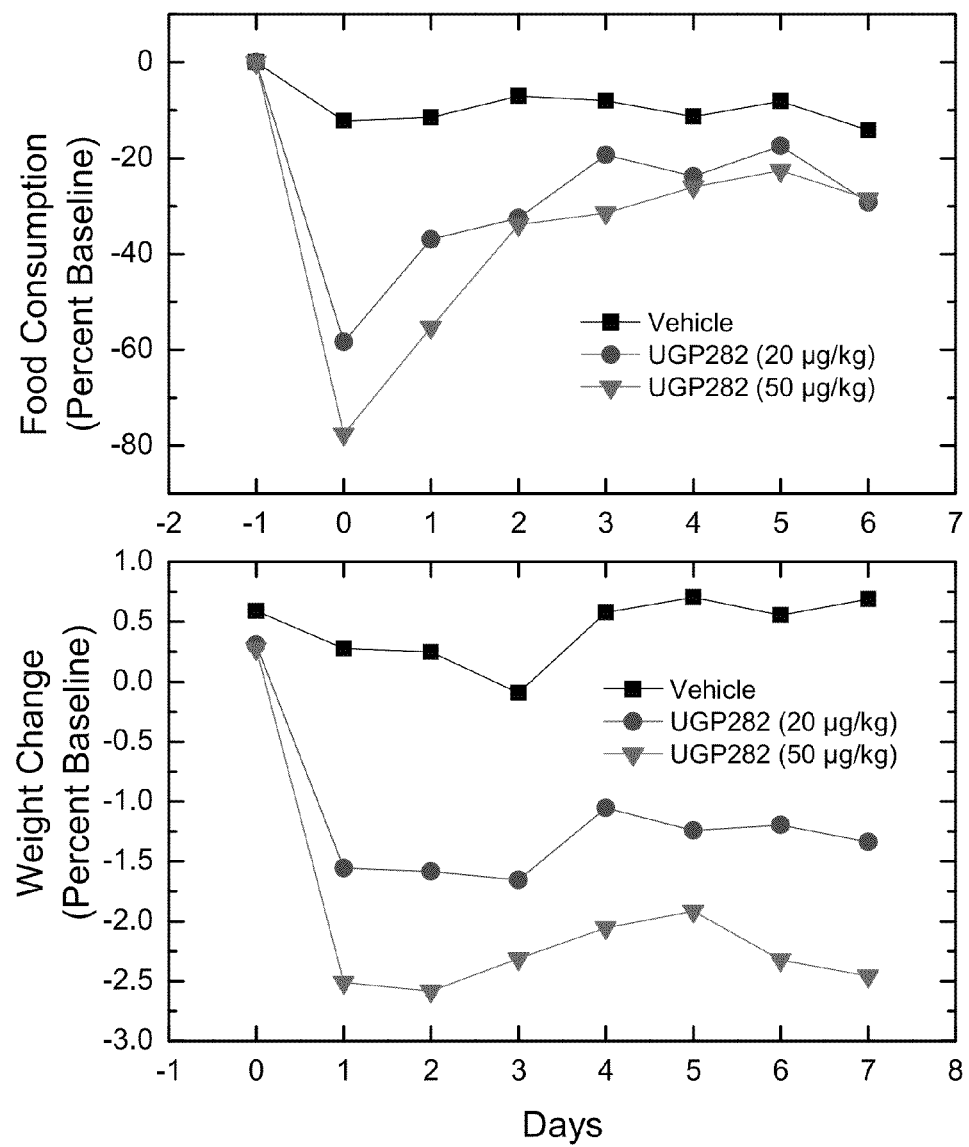
FIGS. 12A and 12B show food consumption (12A) and weight change measurements (12B) for UGP 282 as measured in Example 5.
Figure 13:
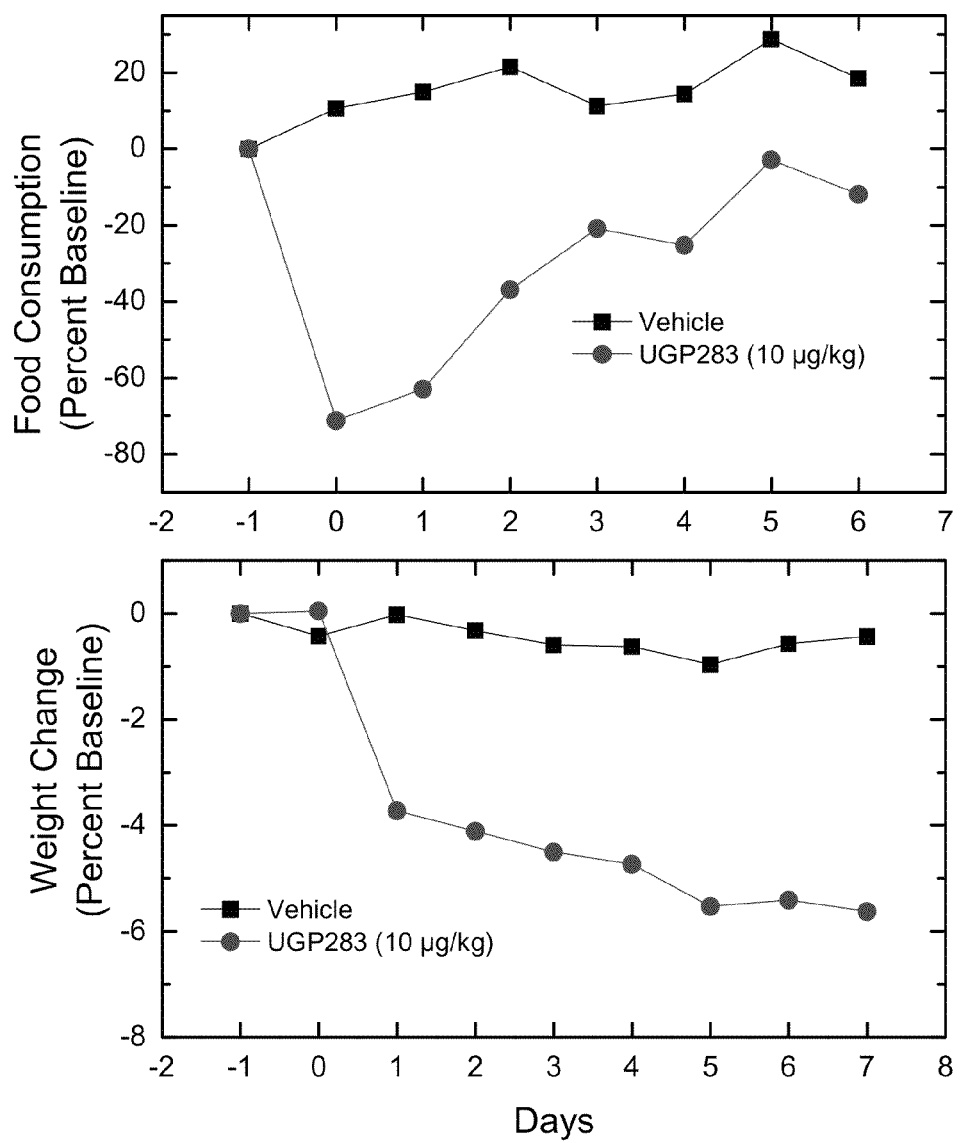
FIGS. 13A and 13B show food consumption (13A) and weight change measurements (13B) for UGP 283 as measured in Example 5.
Figure 14:
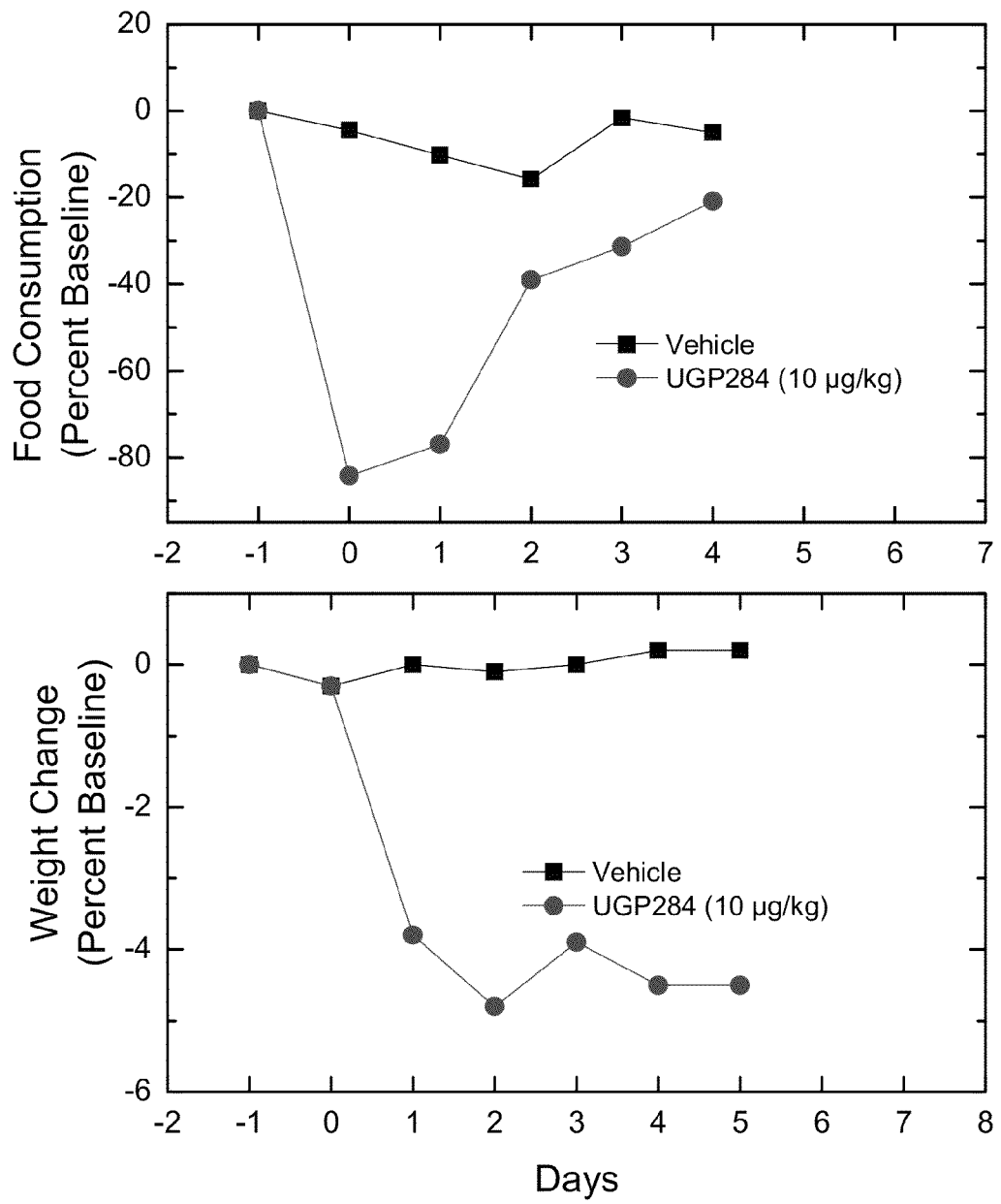
FIGS. 14A and 14B show food consumption (14A) and weight change measurements (14B) for UGP 284 as measured in Example 5.
Figure 15:
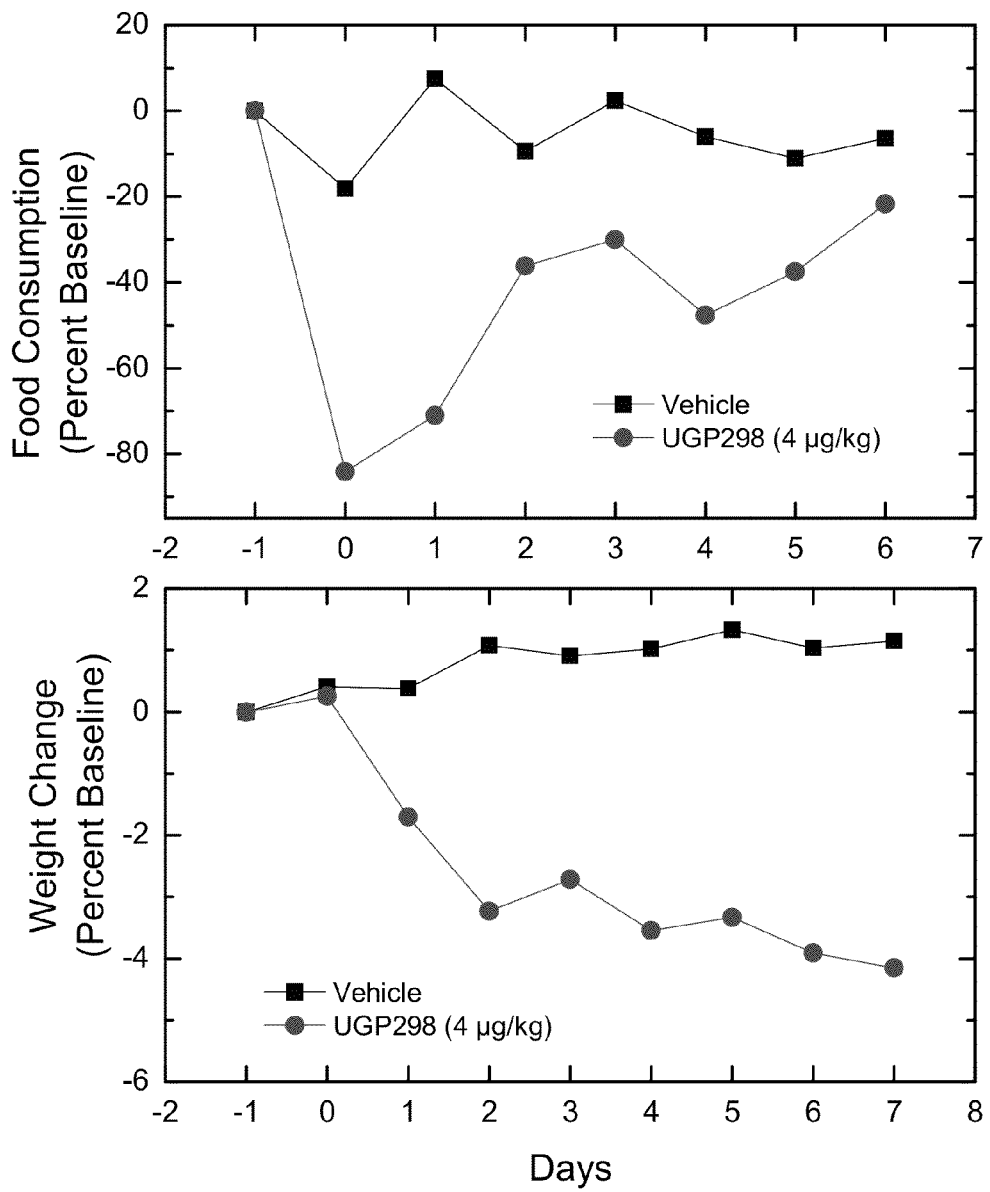
FIGS. 15A and 15B show food consumption (15A) and weight change measurements (15B) for UGP 298 as measured in Example 5.
Figure 16:
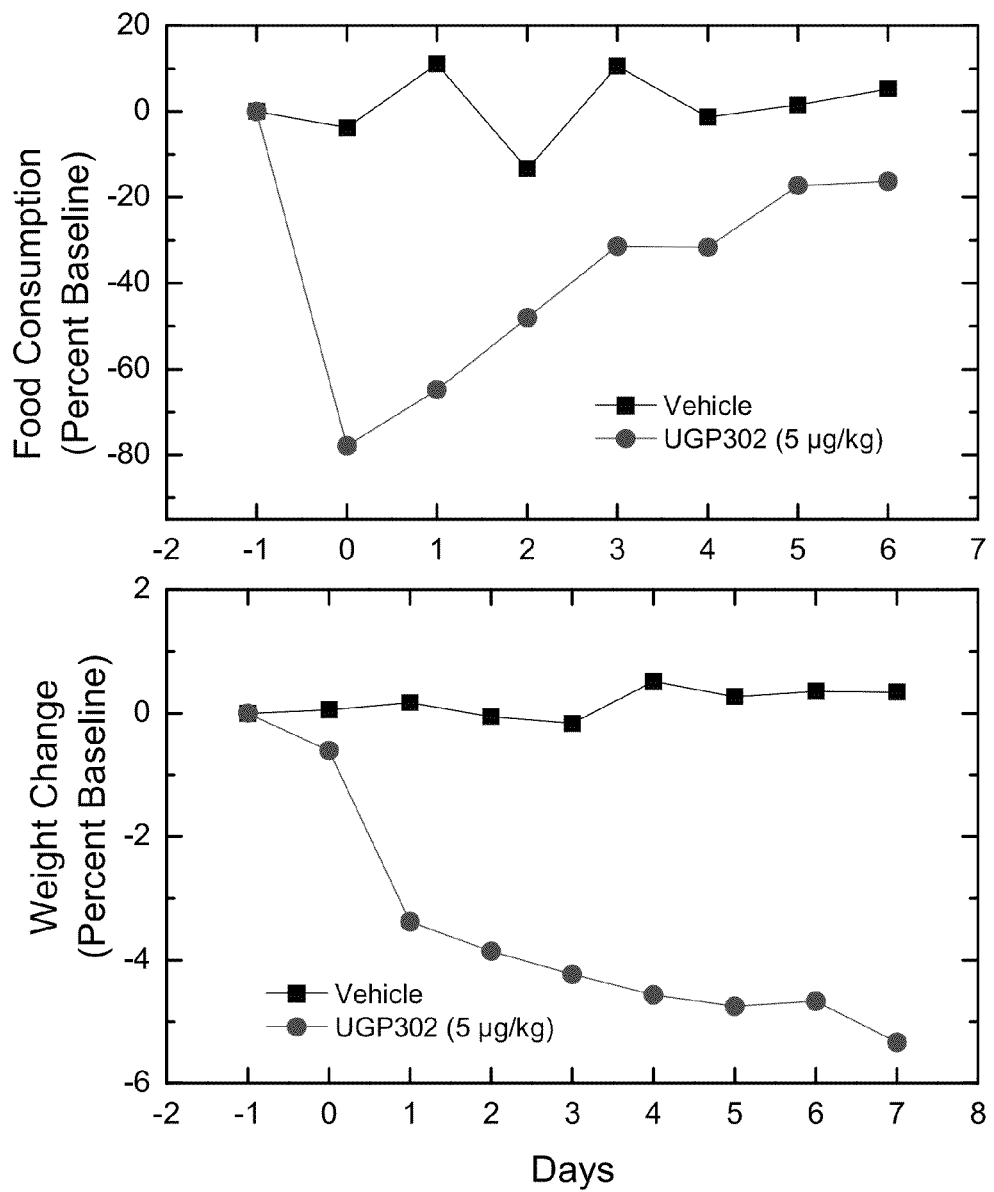
FIGS. 16A and 16B show food consumption (16A) and weight change measurements (16B) for UGP 302 as measured in Example 5.
Figure 17:
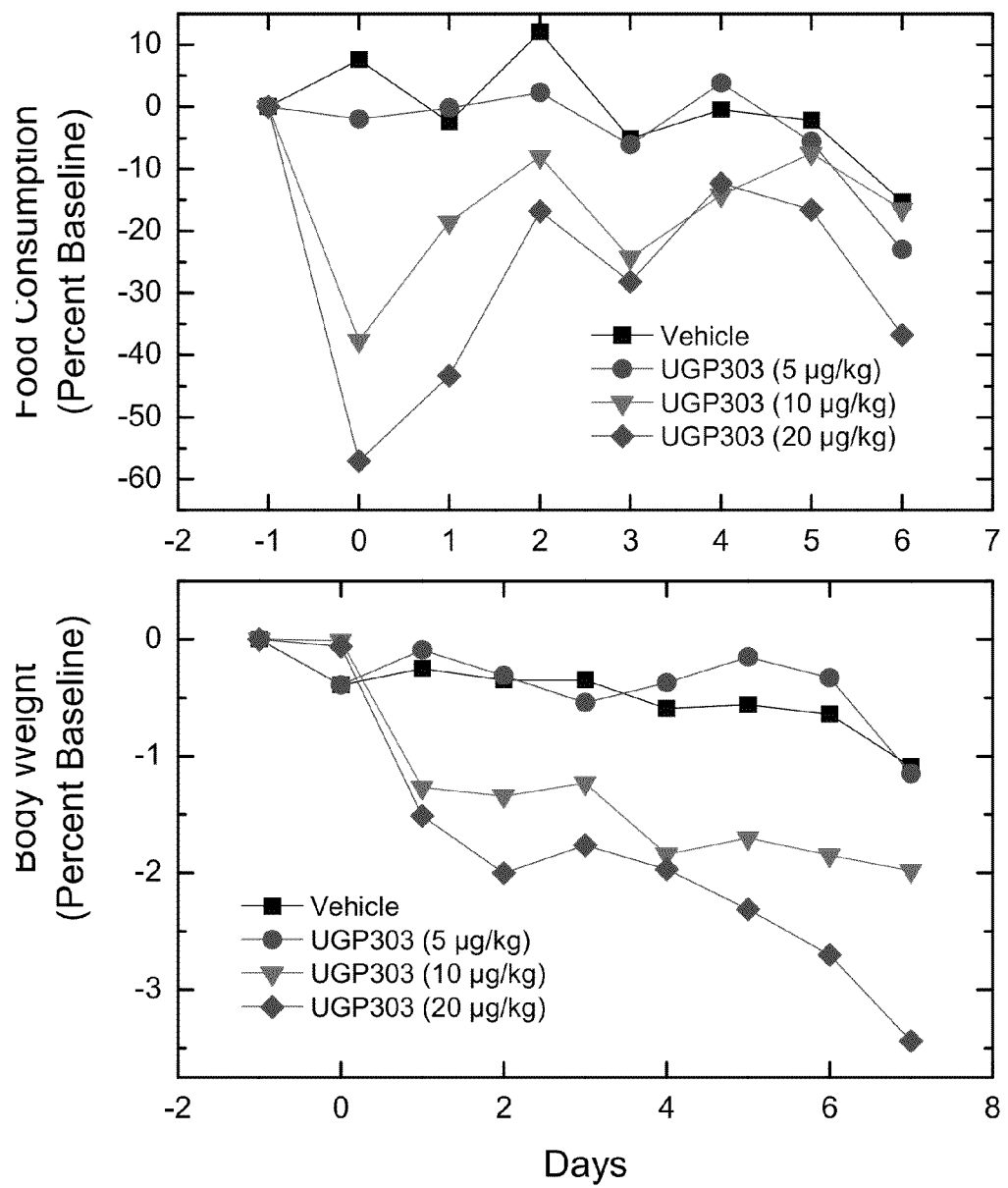
FIGS. 17A and 17B show food consumption (17A) and weight change measurements (17B) for UGP 303 as measured in Example 5.

Binding of sCT Analogs to T47D Cell Calcitonin Receptors sCT analogs at various concentrations were tested in a T47D (human breast epithelial cell line) bioassay. This cell line is known to have the following receptors: calcitonin, androgen, progesterone, glucocrticoid, prolactin and estrogen. The results are presented in FIG. 11 as % cAMP binding relative to sCT which was set at 100% cAMP binding at a concentration of 1000 pg/mL. It can be seen that UGP302 provides the highest level of binding of all the tested compounds and that it provides a higher level of binding than sCT.

Example 5

Food Consumption and Weight Change in Rats Fed sCT Analogs

Male Sprague-Dawley rats were housed individually in cages in which the light/dark cycle was reversed. Rats were allowed to eat ad libitum. Food consumption and rat weights were monitored daily during each study. Rats were injected intramuscularly with a saline placebo or the indicated peptide at the specified dose in saline. The data in the following tables is summarized as the mean change in food consumption relative to the day before treatment began (day-1) and as the mean change in weight relative to the day before treatment began.

The results are shown in FIGS. 12-17. FIGS. 12A and 12B show food consumption (12A) and weight change measurements (12B) for UGP 282 as measured in Example 5.

FIGS. 13A and 13B show food consumption (13A) and weight change measurements (13B) for UGP 283 as measured in Example 5. FIGS. 14A and 14B show food consumption (14A) and weight change measurements (14B) for UGP 284 as measured in Example 5. FIGS. 15A and 15B show food consumption (15A) and weight change measurements (15B) for UGP 298 as measured in Example 5. FIGS. 16A and 16B show food consumption (16A) and weight change measurements (16B) for UGP 302 as measured in Example 5. FIGS. 17A and 17B show food consumption (17A) and weight change measurements (17B) for UGP 303 as measured in Example 5.

It can be seen that all of the tested compounds induce weight loss and reduce feed intake.

Example 6

Markers of Osteoporosis and Osteoarthritis

The effect of sCT/calcitonin mimetic on bone and cartilage loss was studied in DIO rats. The animals were dosed as described in the table below, and 2 hours after treatment blood sampling was done by heated tail venous puncture.

Serum CTX-I levels, as an indication of bone resorption, were measured using the RatLaps™ ELISA, and serum CTX-II levels, as an indication of cartilage degradation, were measured using the Serum PC Cartilaps™ ELISA.

Experimental Groups

| Intervention | Compound | Conc. | Number |
| --- | --- | --- | --- |
| Oral vehicle | 5-CNAC | 150 mg/kg | n = 8 |
| Oral sCT | 5-CNAC + sCT | 150 mg/kg + 1 mg/kg | n = 8 |
| Oral calcitonin mimetic of SEQ ID NO: 18 | 5-CNAC + SEQ ID NO: 15 | 150 mg/kg 1 mg/kg | n = 8 |

Figure 18:
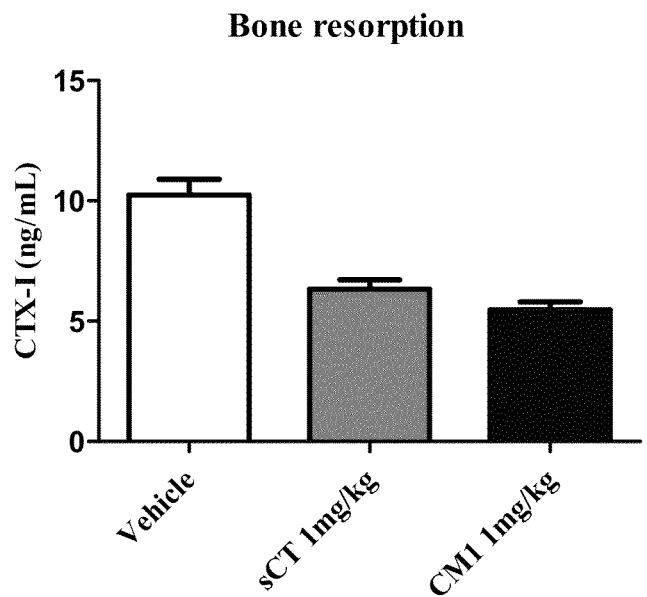
FIGS. 18 and 19 show respectively the reduction of bone resorption and cartilage resorption produced by treatment with UGP302 in rats.
Figure 19:
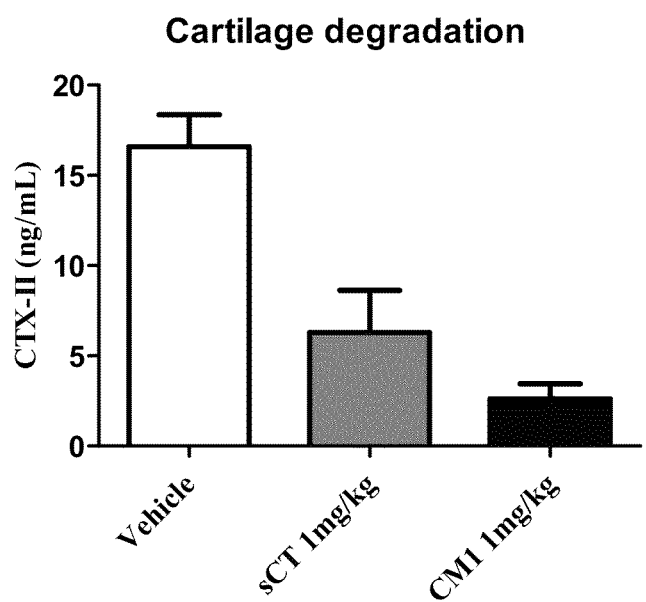

The results are seen in FIGS. 18 and 19, where a calcitonin mimetic of SEQ ID NO: 18 shows a stronger effect in reduction of both bone resorption and cartilage degradation than does sCT.

In some embodiments, a peptide of the present disclosure has a sequence selected from SEQ ID NO:11, SEQ ID NO:12, SEQ ID NO:13, SEQ ID NO:14, SEQ ID NO:15, SEQ ID NO:17 and SEQ ID NO:18.

In some embodiments, a method includes administering to a patient an effective amount of a peptide selected from the group consisting of: SEQ ID NO:11, SEQ ID NO:12, SEQ ID NO:13, SEQ ID NO:14, SEQ ID NO:15, and SEQ ID NO:17 to effect a weight reduction in the patient.

In some embodiments, a method includes administering to a patient an effective amount of a peptide selected from the group consisting of: SEQ ID NO:11, SEQ ID NO:12, SEQ ID NO:13, SEQ ID NO:14, SEQ ID NO:15, and SEQ ID NO:17 to effect postprandial glycemic control in the patient.

In some embodiments, a method includes administering to the patient an effective amount of a peptide selected from the group consisting of: SEQ ID NO:11, SEQ ID NO:12, SEQ ID NO:13, SEQ ID NO:14, SEQ ID NO:15, and SEQ ID NO:17 to effect an improvement in glycemic control in the patient.

In some embodiments, a method includes administering to a patient an effective amount of a peptide of SEQ ID NO:18 having the sequence $C_m$SNLSTCVLGKLSQELHKLQ-TYPRTDVGANXaaXaa$_a$ so as to reduce at least one of bone resorption and cartilage degradation in the patient.

All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method comprising administering to the patient an effective amount of a peptide selected from the group consisting of:

AcCSNLSTCVLGKLSQELHKLQTYPRTDVGANAP-NH2 SEQ ID NO:15,

AcCSNLSTCVLGRLSQELHRLQTFPRTD-VGANTAcY SEQ ID NO:12, and

SuccCSNLSTCVLGKLSQELHKLQ-TYPRTDVGANAY-NH2 SEQ ID NO:17 to effect a weight reduction in the patient.

2. The method of claim 1, wherein the peptide is formulated for enteral administration.

3. The method of claim 1, wherein the peptide is formulated for parenteral administration.

4. The method of claim 1, wherein the peptide is formulated with a carrier for oral administration, and wherein the carrier increases the oral bioavailability of the peptide.

5. The method of claim 4, wherein the carrier comprises N-(5-chlorosalicyloyl)-8-aminocaprylic acid (5-CNAC), sodium salt of 10-(2-Hydroxybenzamido)decanoic acid (SNAD), or sodium salt of N-(8-[2-hydroxybenzoyl]amino) caprylic acid (SNAG).

6. The method of claim 1, wherein the peptide is formulated in a pharmaceutical composition for oral administration comprising coated citric acid particles, and wherein the coated citric acid particles increases the oral bioavailability of the peptide.

7. A method comprising administering to a patient an effective amount of a peptide selected from the group consisting of:

AcCSNLSTCVLGKLSQELHKLQTYPRTDVGANAP-NH2 SEQ ID NO:15,

AcCSNLSTCVLGRLSQELHRLQTFPRTD-VGANTAcY SEQ ID NO:12, and

SuccCSNLSTCVLGKLSQELHKLQ-TYPRTDVGANAY-NH2 SEQ ID NO:17 to effect postprandial glycemic control in the patient.

8. The method of claim 7, wherein the peptide is formulated for enteral administration.

9. The method of claim 7, wherein the peptide is formulated for parenteral administration.

10. The method of claim 7, wherein the peptide is formulated with a carrier for oral administration.

11. The method of claim 10, wherein the carrier comprises N-(5-chlorosalicyloyl)-8-aminocaprylic acid (5-CNAC), sodium salt of 10-(2-Hydroxybenzamido)decanoic acid (SNAD), or sodium salt of N-(8-[2-hydroxybenzoyl]amino) caprylic acid (SNAG).

12. The method of claim 7, wherein the peptide is formulated in a pharmaceutical composition for oral administration comprising coated citric acid particles, and wherein the coated citric acid particles increases the oral bioavailability of the peptide.

13. A method comprising administering to a patient an effective amount of a peptide selected from the group consisting of:

AcCSNLSTCVLGKLSQELHKLQTYPRTDVGANAP-NH2 SEQ ID NO:15,

AcCSNLSTCVLGRLSQELHRLQTFPRTD-VGANTAcY SEQ ID NO:12, and

SuccCSNLSTCVLGKLSQELHKLQ-TYPRTDVGANAY-NH2 SEQ ID NO:17 to effect an improvement in glycemic control in the patient.

14. The method of claim 13, wherein the peptide is formulated for enteral administration.

15. The method of claim 13, wherein the peptide is formulated for parenteral administration.

16. The method of claim 12, wherein the peptide is formulated with a carrier for oral administration.

17. The method of claim 16, wherein the carrier comprises N-(5-chlorosalicyloyl)-8-aminocaprylic acid (5-CNAC), sodium salt of 10-(2-Hydroxybenzamido)decanoic acid (SNAD), or sodium salt of N-(8-[2-hydroxybenzoyl]amino) caprylic acid (SNAG).

18. The method of claim 12, wherein the peptide is formulated in a pharmaceutical composition for oral administration comprising coated citric acid particles, and wherein the coated citric acid particles increases the oral bioavailability of the peptide.

* * * * *

SEQUENCE LISTING

<160> NUMBER OF SEQ ID NOS: 18

<210> SEQ ID NO 1
<211> LENGTH: 32
<212> TYPE: PRT
<213> ORGANISM: salmon

<400> SEQUENCE: 1

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

```
<210> SEQ ID NO 2
<211> LENGTH: 32
<212> TYPE: PRT
<213> ORGANISM: Mouse

<400> SEQUENCE: 2

Cys Gly Asn Leu Ser Thr Cys Met Leu Gly Thr Tyr Thr Gln Asp Leu
1               5                   10                  15

Asn Lys Phe His Thr Phe Pro Gln Thr Ser Ile Gly Val Glu Ala Pro
            20                  25                  30

<210> SEQ ID NO 3
<211> LENGTH: 32
<212> TYPE: PRT
<213> ORGANISM: Chicken

<400> SEQUENCE: 3

Cys Ala Ser Leu Ser Thr Cys Val Leu Gly Lys Leu Ser Gln Glu Leu
1               5                   10                  15

His Lys Leu Gln Thr Tyr Pro Arg Thr Asp Val Gly Ala Gly Thr Pro
            20                  25                  30

<210> SEQ ID NO 4
<211> LENGTH: 32
<212> TYPE: PRT
<213> ORGANISM: Eel

<400> SEQUENCE: 4

Cys Ser Asn Leu Ser Thr Cys Val Leu Gly Lys Leu Ser Gln Glu Leu
1               5                   10                  15

His Lys Leu Gln Thr Tyr Pro Arg Thr Asp Val Gly Ala Gly Thr Pro
            20                  25                  30

<210> SEQ ID NO 5
<211> LENGTH: 32
<212> TYPE: PRT
<213> ORGANISM: Rat

<400> SEQUENCE: 5

Cys Gly Asn Leu Ser Thr Cys Met Leu Gly Thr Tyr Thr Gln Asp Leu
1               5                   10                  15

Asn Lys Phe His Thr Phe Pro Gln Thr Ser Ile Gly Val Gly Ala Pro
            20                  25                  30

<210> SEQ ID NO 6
<211> LENGTH: 32
<212> TYPE: PRT
<213> ORGANISM: Horse

<400> SEQUENCE: 6

Cys Ser Asn Leu Ser Thr Cys Val Leu Gly Thr Tyr Thr Gln Asp Leu
1               5                   10                  15

Asn Lys Phe His Thr Phe Pro Gln Thr Ala Ile Gly Val Gly Ala Pro
            20                  25                  30

<210> SEQ ID NO 7
<211> LENGTH: 32
<212> TYPE: PRT
<213> ORGANISM: Canine
```

```
<400> SEQUENCE: 7

Cys Ser Asn Leu Ser Thr Cys Val Leu Gly Thr Tyr Ser Lys Asp Leu
1               5                   10                  15

Asn Asn Phe His Thr Phe Ser Gly Ile Gly Phe Gly Ala Glu Thr Pro
            20                  25                  30

<210> SEQ ID NO 8
<211> LENGTH: 32
<212> TYPE: PRT
<213> ORGANISM: Canine

<400> SEQUENCE: 8

Cys Ser Asn Leu Ser Thr Cys Val Leu Gly Thr Tyr Thr Gln Asp Leu
1               5                   10                  15

Asn Lys Phe His Thr Phe Pro Gln Thr Ala Ile Gly Val Gly Ala Pro
            20                  25                  30

<210> SEQ ID NO 9
<211> LENGTH: 32
<212> TYPE: PRT
<213> ORGANISM: Porcine

<400> SEQUENCE: 9

Cys Ser Asn Leu Ser Thr Cys Val Leu Ser Ala Tyr Trp Arg Asn Leu
1               5                   10                  15

Asn Asn Phe His Arg Phe Ser Gly Met Gly Phe Gly Pro Glu Thr Pro
            20                  25                  30

<210> SEQ ID NO 10
<211> LENGTH: 32
<212> TYPE: PRT
<213> ORGANISM: Human

<400> SEQUENCE: 10

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 11
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (32)..(32)
<223> OTHER INFORMATION: AMIDATION

<400> SEQUENCE: 11

Cys Ser Asn Leu Ser Thr Cys Val Leu Gly Lys Leu Ser Gln Glu Leu
1               5                   10                  15

His Lys Leu Gln Thr Tyr Pro Arg Thr Asp Val Gly Ala Asn Thr Tyr
            20                  25                  30

<210> SEQ ID NO 12
<211> LENGTH: 32
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (32)..(32)
<223> OTHER INFORMATION: ACETYLATION

<400> SEQUENCE: 12

Cys Ser Asn Leu Ser Thr Cys Val Leu Gly Arg Leu Ser Gln Glu Leu
1               5                   10                  15

His Arg Leu Gln Thr Phe Pro Arg Thr Asp Val Gly Ala Asn Thr Tyr
            20                  25                  30

<210> SEQ ID NO 13
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: propionyl
<220> FEATURE:
<221> NAME/KEY: MOD_RES
<222> LOCATION: (32)..(32)
<223> OTHER INFORMATION: AMIDATION

<400> SEQUENCE: 13

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 14
<211> LENGTH: 32
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: Succinyl
<220> FEATURE:
<221> NAME/KEY: MOD_RES
<222> LOCATION: (32)..(32)
<223> OTHER INFORMATION: AMIDATION

<400> SEQUENCE: 14

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 15
<211> LENGTH: 32
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: (1)..(1)
<223> OTHER INFORMATION: ACETYLATION
```

```
<220> FEATURE:
<221> NAME/KEY: MOD_RES
<222> LOCATION: (32)..(32)
<223> OTHER INFORMATION: AMIDATION

<400> SEQUENCE: 15

Cys Ser Asn Leu Ser Thr Cys Val Leu Gly Lys Leu Ser Gln Glu Leu
1               5                   10                  15

His Lys Leu Gln Thr Tyr Pro Arg Thr Asp Val Gly Ala Asn Ala Pro
            20                  25                  30

<210> SEQ ID NO 16
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (33)..(33)
<223> OTHER INFORMATION: AMIDATION

<400> SEQUENCE: 16

Lys Cys Ser Asn Leu Ser Thr Cys Val Leu Gly Lys Leu Ser Gln Glu
1               5                   10                  15

Leu His Lys Leu Gln Thr Tyr Pro Arg Thr Asp Val Gly Ala Asn Thr
            20                  25                  30

Tyr

<210> SEQ ID NO 17
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Succinyl
<220> FEATURE:
<221> NAME/KEY: MOD_RES
<222> LOCATION: (32)..(32)
<223> OTHER INFORMATION: AMIDATION

<400> SEQUENCE: 17

Cys Ser Asn Leu Ser Thr Cys Val Leu Gly Lys Leu Ser Gln Glu Leu
1               5                   10                  15

His Lys Leu Gln Thr Tyr Pro Arg Thr Asp Val Gly Ala Asn Ala Tyr
            20                  25                  30

<210> SEQ ID NO 18
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Cysteine can be modified with an acetyl group,
      propionyl group, or succinyl group.
<220> FEATURE:
<221> NAME/KEY: MISC_FEATURE
<222> LOCATION: (31)..(31)
<223> OTHER INFORMATION: Xaa can be any naturally occurring amino acid
<220> FEATURE:
<221> NAME/KEY: MISC_FEATURE
<222> LOCATION: (32)..(32)
<223> OTHER INFORMATION: Xaa can be any naturally occurring amino acid
```

```
<220> FEATURE:
<221> NAME/KEY: MOD_RES
<222> LOCATION: (32)..(32)
<223> OTHER INFORMATION: Optionally amidated

<400> SEQUENCE: 18

Cys Ser Asn Leu Ser Thr Cys Val Leu Gly Lys Leu Ser Gln Glu Leu
1               5                   10                  15

His Lys Leu Gln Thr Tyr Pro Arg Thr Asp Val Gly Ala Asn Xaa Xaa
            20                  25                  30
```